(12) United States Patent
Currie et al.

(10) Patent No.: US 8,364,228 B2
(45) Date of Patent: Jan. 29, 2013

(54) APPARTUS AND METHOD FOR CONTINUOUS REAL-TIME TRACE BIOMOLECULAR SAMPLING, ANALYSIS, AND DELIVERY

(75) Inventors: John Frederick Currie, Bethesda, MD (US); Makarand Paranjape, Silver Spring, MD (US)

(73) Assignee: Flexible Medical Systems, LLC, Rockville, MD (US)

( * ) Notice: Subject to any disclaimer, the term of this patent is extended or adjusted under 35 U.S.C. 154(b) by 599 days.

(21) Appl. No.: 11/721,287

(22) PCT Filed: Dec. 9, 2005

(86) PCT No.: PCT/US2005/044287
§ 371 (c)(1),
(2), (4) Date: May 19, 2009

(87) PCT Pub. No.: WO2006/063063
PCT Pub. Date: Jun. 15, 2006

(65) Prior Publication Data
US 2009/0281404 A1    Nov. 12, 2009

(51) Int. Cl.
*A61B 5/05* (2006.01)
(52) U.S. Cl. ........ 600/345; 600/309; 600/346; 600/347; 600/365
(58) Field of Classification Search .................. 600/306, 600/309, 345–348, 365, 368, 372, 382, 386–397, 600/573, 575, 584; 604/19–20
See application file for complete search history.

(56) References Cited

U.S. PATENT DOCUMENTS

| | | | |
|---|---|---|---|
| 4,526,176 | A | 7/1985 | Bremer et al. |
| 4,775,361 | A | 10/1988 | Jacques et al. |
| 4,821,733 | A | 4/1989 | Peck |
| 4,909,256 | A | 3/1990 | Peck |
| 5,019,034 | A | 5/1991 | Weaver et al. |
| 5,123,902 | A | 6/1992 | Muller et al. |
| 5,149,629 | A | 9/1992 | Rishpon et al. |
| 5,176,881 | A | 1/1993 | Sepaniak et al. |
| 5,203,327 | A | 4/1993 | Schoendorfer et al. |
| 5,284,748 | A | 2/1994 | Mroczkowski et al. |

(Continued)

FOREIGN PATENT DOCUMENTS
EP       1 003 033 A1     5/2000
WO       WO 97/42882     11/1997

OTHER PUBLICATIONS

Currie et al., "Novel Non-Intrusive Trans-Dermal Remote Wireless Micro-Fluidic Monitoring System Applied to Continuous Glucose and Lactate Assays for Casualty Care and Combat Readiness," NATO: RTO-MP-HFM-109, pp. 24-1-24-17 (2004).*

(Continued)

*Primary Examiner* — Rene Towa
(74) *Attorney, Agent, or Firm* — The Marbury Law Group, PLLC

(57) ABSTRACT

A system and method for transdermal sampling wherein at least one pair of sample electrodes is adapted to provide voltage pulses capable of creating capillary openings in a subject's stratum corneum. Methods for using a transdermal sampling system by creating capillary openings in a subject's stratum corneum via the application of a series of voltage pulses to the stratum corneum and contacting at least a portion of at least one of the sample electrodes with interstitial fluid from the capillary openings are also presented.

21 Claims, 22 Drawing Sheets

U.S. PATENT DOCUMENTS

| | | | |
|---|---|---|---|
| 5,330,527 | A | 7/1994 | Montecalvo et al. |
| 5,362,307 | A | 11/1994 | Guy et al. |
| 5,366,454 | A | 11/1994 | Currie et al. |
| 5,380,272 | A | 1/1995 | Gross |
| 5,458,140 | A | 10/1995 | Eppstein et al. |
| 5,711,861 | A | 1/1998 | Ward et al. |
| 5,722,397 | A | 3/1998 | Eppstein |
| 5,730,714 | A | 3/1998 | Guy et al. |
| 5,885,211 | A | 3/1999 | Eppstein et al. |
| 5,983,131 | A * | 11/1999 | Weaver et al. ............ 604/20 |
| 6,022,316 | A * | 2/2000 | Eppstein et al. ........... 600/309 |
| 6,056,738 | A | 5/2000 | Marchitto et al. |
| 6,124,597 | A | 9/2000 | Shehada et al. |
| 6,144,869 | A * | 11/2000 | Berner et al. ............. 600/347 |
| 6,233,471 | B1 | 5/2001 | Berner et al. |
| 6,270,651 | B1 | 8/2001 | Essalik et al. |
| 6,342,037 | B1 | 1/2002 | Roe et al. |
| 6,393,318 | B1 | 5/2002 | Conn et al. |
| 6,464,687 | B1 | 10/2002 | Ishikawa et al. |
| 6,572,542 | B1 | 6/2003 | Houben et al. |
| 6,597,946 | B2 | 7/2003 | Avrahami et al. |
| 6,887,202 | B2 | 5/2005 | Currie et al. |
| 6,922,578 | B2 * | 7/2005 | Eppstein et al. ........... 600/347 |
| 6,922,586 | B2 | 7/2005 | Davies |
| 7,001,495 | B2 | 2/2006 | Essalik et al. |
| 7,826,981 | B2 | 11/2010 | Goode, Jr. et al. |
| 2001/0052459 | A1 | 12/2001 | Essalik et al. |
| 2003/0130616 | A1 | 7/2003 | Steil et al. |
| 2003/0208152 | A1 * | 11/2003 | Avrahami et al. ........... 604/20 |
| 2003/0225362 | A1 * | 12/2003 | Currie et al. ............ 604/20 |
| 2004/0157319 | A1 | 8/2004 | Keen |
| 2004/0193219 | A1 * | 9/2004 | Asano et al. .............. 607/1 |
| 2004/0253304 | A1 * | 12/2004 | Gross et al. ............ 424/451 |
| 2005/0069454 | A1 * | 3/2005 | Bell ................... 422/68.1 |
| 2005/0182307 | A1 | 8/2005 | Currie et al. |
| 2005/0226921 | A1 * | 10/2005 | Kortzebom ............ 424/449 |
| 2006/0241514 | A1 | 10/2006 | Davies |
| 2009/0281404 | A1 | 11/2009 | Currie et al. |

OTHER PUBLICATIONS

International Search Report, PCT/US05/44287, 1 page, Aug. 28, 2006.

Written Opinion of the International Searching Authority, PCT/US05/44287, 4 pages, Aug. 28, 2006.

Preliminary Examination Report, PCT/US01/17081, 5 pages, Sep. 17, 2004.

Balabanova et al., "Detection of Drugs in Sweat (Nachweis von Drogen im Schweiβ)," Beitr. Gerichtl. Med., vol. 48, pp. 45-49, 1990.

Henderson et al., "Excretion of Methadone and Metabolites in Human Sweat," Research Communications in Chemical Pathology and pharmacology, vol. 5, No. 1, pp. 1-8, Jan. 1973.

Peck et al., "Outward Transcutaneous Chemical Migration: Impliations for Diagnostics and Dosimetry", Skin Pharmacol., vol. 1, No. 1, pp. 14-23, 1988.

Phillips et al., "A Sweat-Patch Test for Alcohol Consumption: Evaluation in Continuous and Episodic Drinkers", Alcohol: clinical and Experimental research, vol. 4, No. 4, pp. 391-395, 1980.

"SpectRx An Innovactive Medical Technology Company" [online], Copyright 2004, 1 page, Retrieved from the Internet: http://www.spectrx.com.

Schneider et al., "B-Fit μSystem: Bio-Flips Integrable Transdermal MicroSystem", ARO Workshop on Biomolecular Signaling, Energy Transfer, and Transduction Processes, Cashiers, NC, 16 pages, May 14-17, 2000.

Smith et al., "Cocaine in Hair, Saliva, Skin Swabs, and Urine of Cocaine Users' Children", Forensic Science International, vol. 83, pp. 179-189, 1996.

Nijdam, A.J., et al., "Fluidic encapsulation in SU-8 [micro]-reservoirs with [micro]-fluidic through-chip channels", Sensors and Actuators A, vol. 120, Apr. 29, 2005, p. 172-183.

Gadre et al., "Fabrication of a fluid encapsulated dermal patch using multilayered SU-8," Sensors and Actuators A: Physical, 114(2-3):478-485 (2004).

Paranjape et al., "A PDMS dermal patch for non-intrusive transdermal glucose sensing," Sensors and Actuators A: Physical, 104(3):195-204 (2003).

European Search Report dated Apr. 29, 2009, issued in US Application No. PCT/US2006023194, mailed on May 13, 2009.

Information Disclosure Statement filed Aug. 12, 2009 in related U.S. Appl. No. 12/096,769.

Non-Final Office Action with List of References cited by the Examiner mailed on Aug. 11, 2011 in related U.S. Appl. No. 12/096,769.

Information Disclosure Statement filed Sep. 22, 2008 in related U.S. Appl. No. 12/096,769.

Information Disclosure Statement filed Jun. 18, 2012 in related U.S. Appl. No. 13/294,368.

Information Disclosure Statement filed Sep. 11, 2012 in related U.S. Appl. No. 13/609,838.

Notice of Allowance and Fee(s) Due with Reasons for Allowance, issued Aug. 30, 2012 in related U.S. Appl. No. 12/096,769.

International Search Report with Written Opinion, PCT/US2011/06558, 15 pages, issued Jul. 25, 2012, mailed Jul. 27, 2012.

* cited by examiner

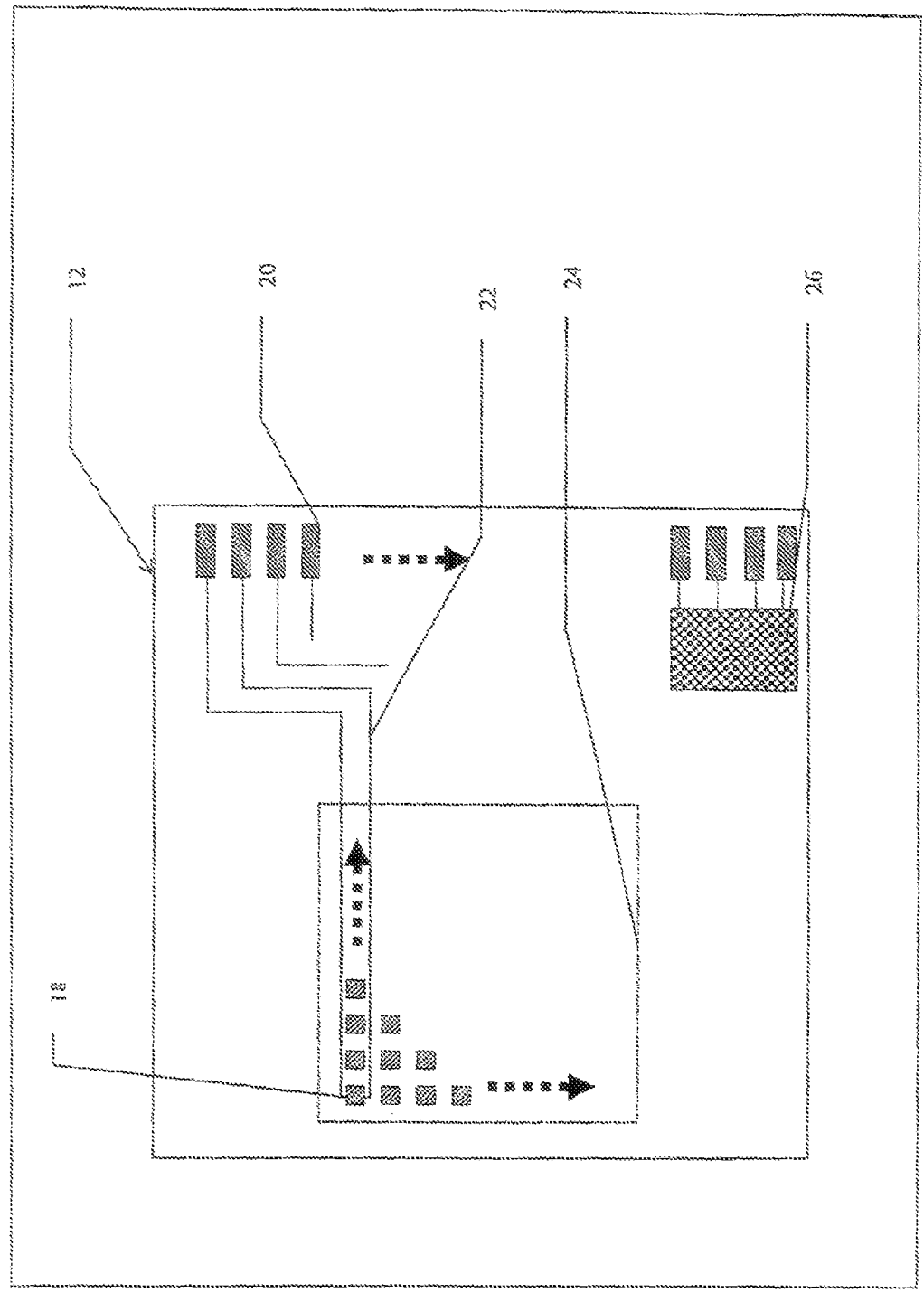

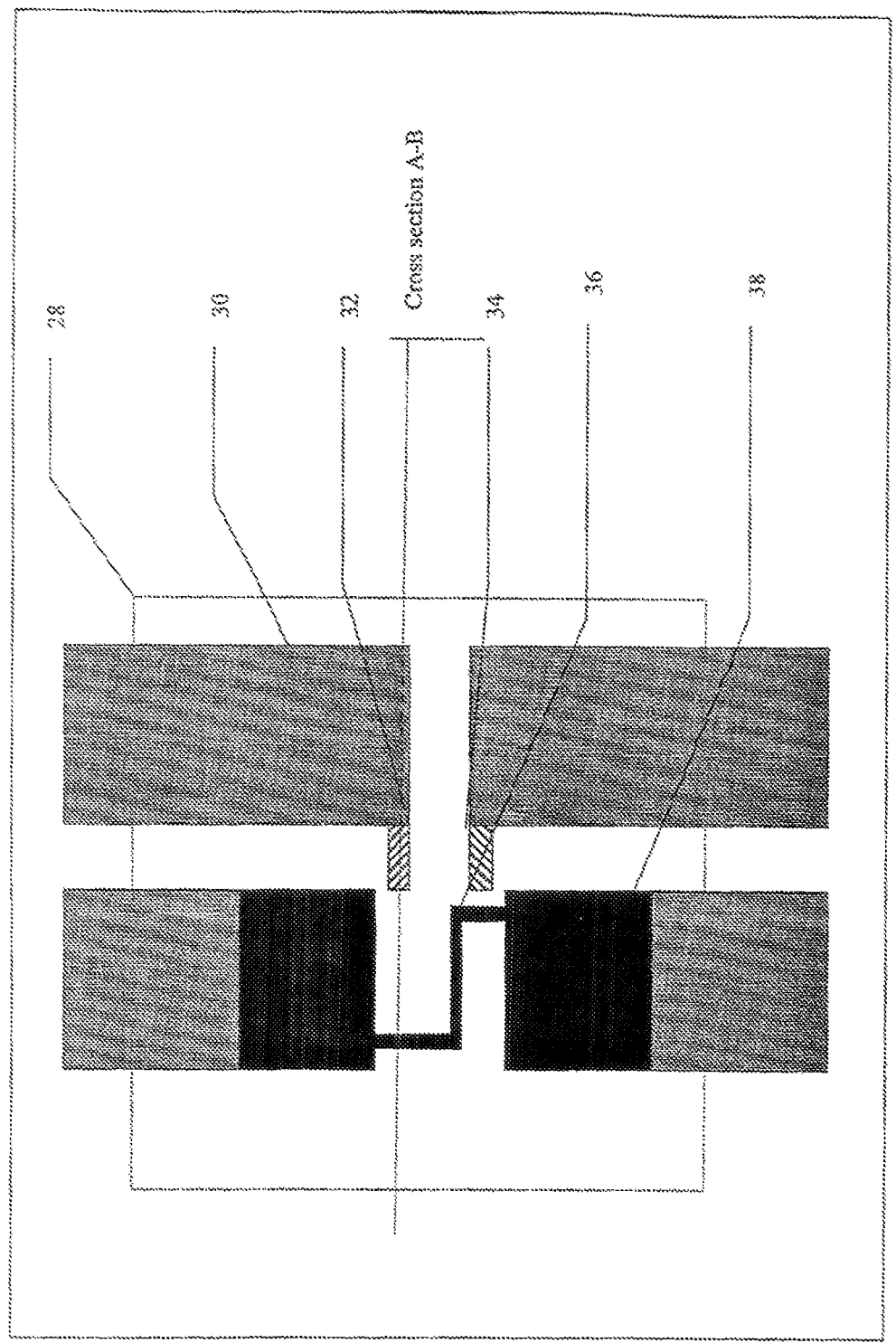

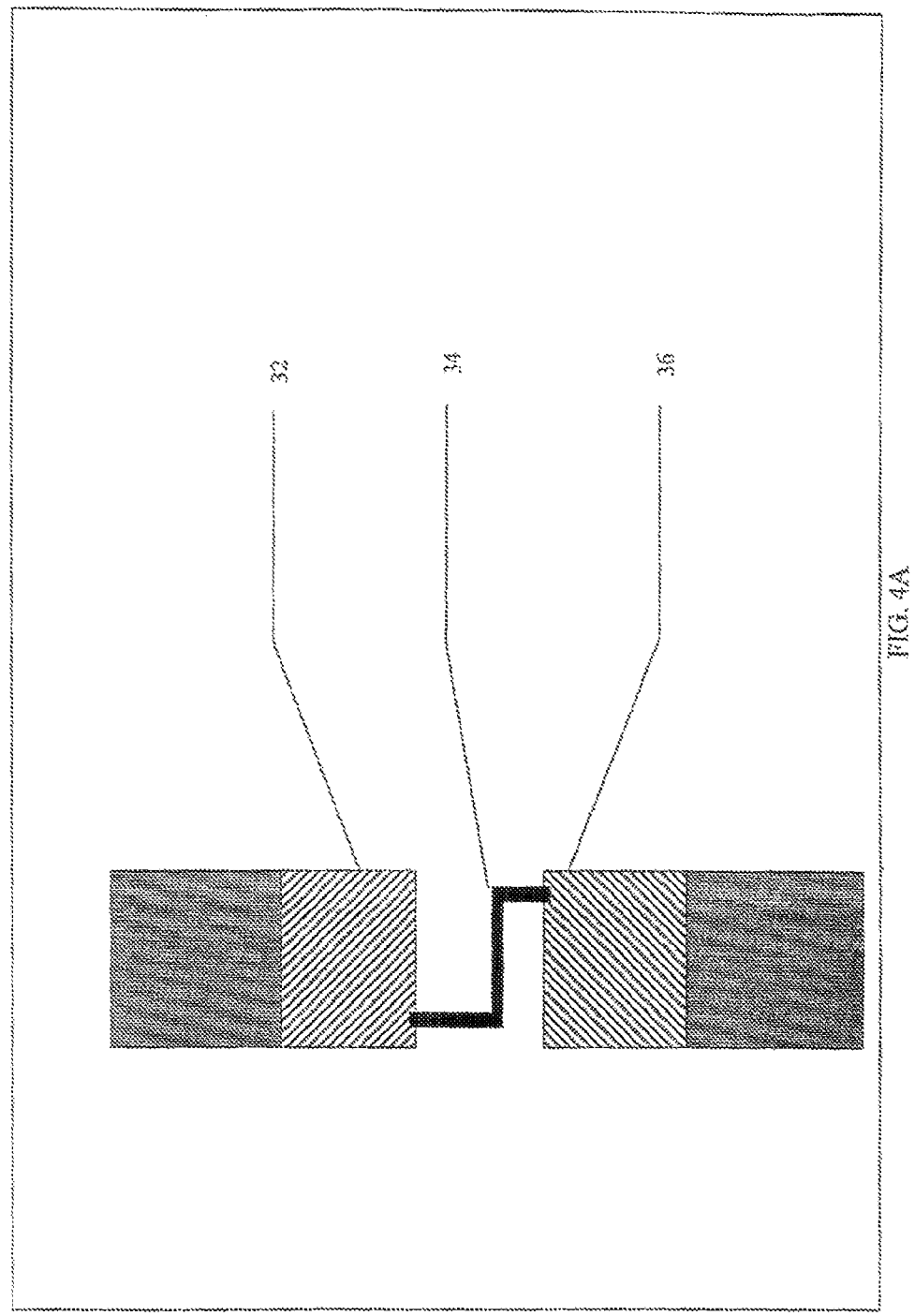

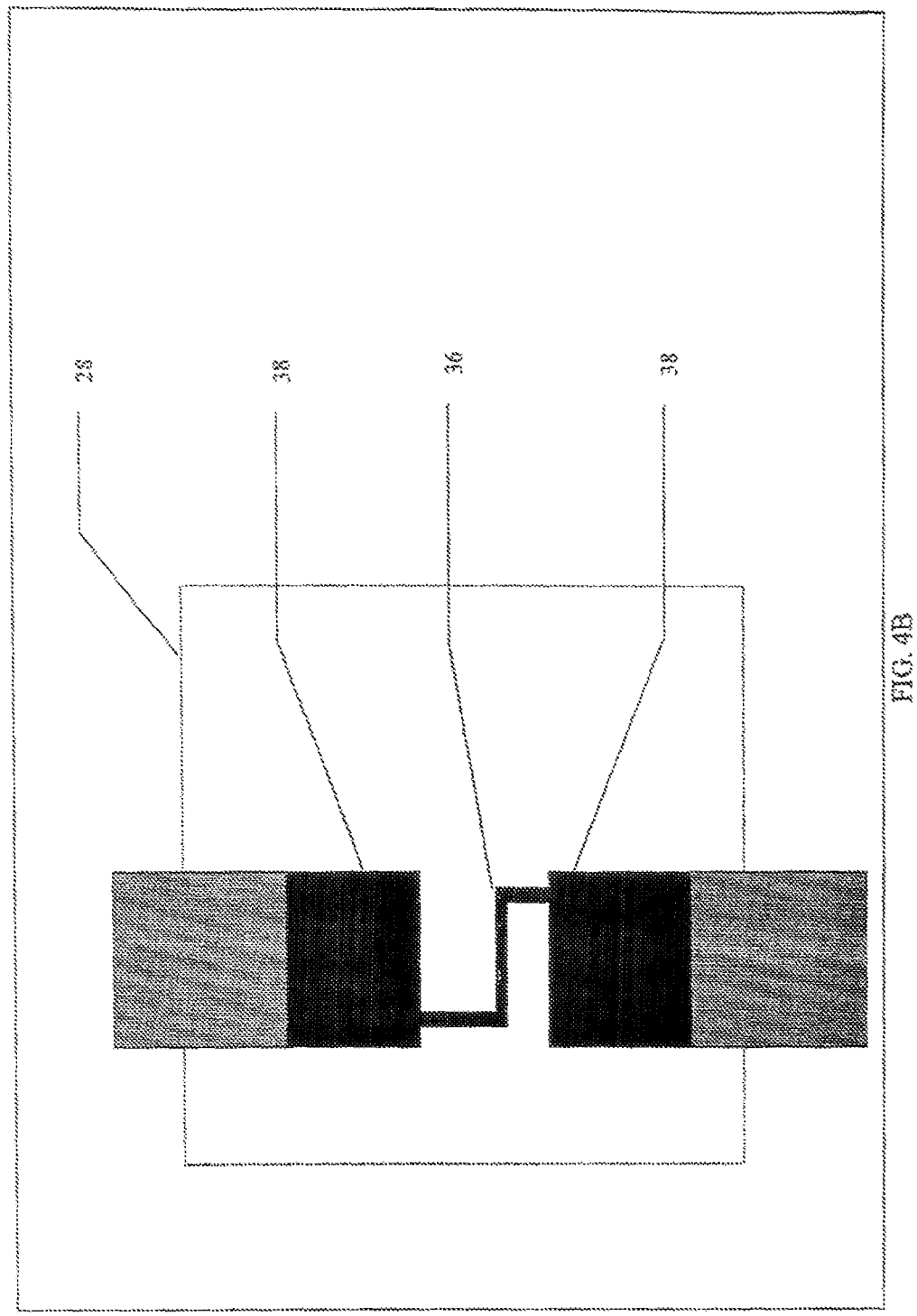

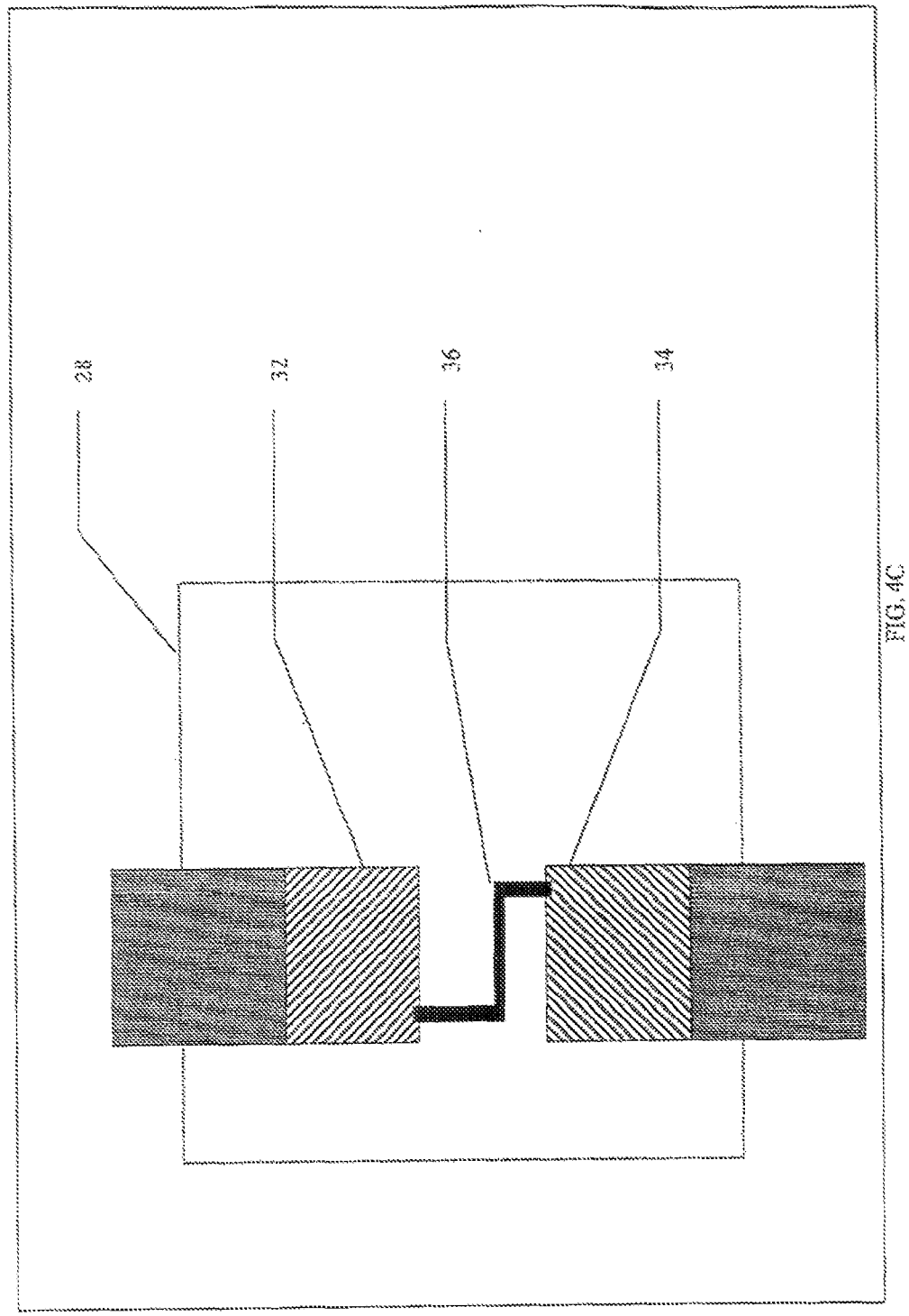

APPARATUS AND METHOD FOR CONTINUOUS REAL-TIME TRACE BIOMOLECULAR SAMPLING, ANALYSIS, AND DELIVERY

CROSS REFERENCE TO APPLICATIONS

This application is a national phase of International Patent Applications No. PCT/US2005/044287, filed Dec. 9, 2005, which claims priority to U.S. Provisional Patent Application No. 60/634,783, filed on Dec. 9, 2004, the contents of which are hereby incorporated by reference.

TECHNICAL FIELD

The present invention relates to the field of portable bio-medical and bio-molecular monitoring. More specifically, the present invention relates to a method, apparatus, and system for minimally invasive, continuous real-time trace bio-molecular sampling, analysis and delivery.

BACKGROUND ART

Non-invasive, transdermal sampling of body fluids has long been a goal of medical research.

Prior an attempts to achieve this goal ate described in, tor instance U.S. Pat. No. 6,887,202 issued on May 3, 2005 to Currie et al. entitled "Systems and Methods for Monitoring health and Delivering Drugs Transdermally" the contents of which are hereby incorporated by reference.

The prior attempts at transdermal sampling have typically been characterized by making relatively large holes in the outermost layer of the epidermis, namely the stratum corneum which is effectively the surface of the skin and is composed mainly of dead cells that lack nuclei. The holes are typically made by heat or laser ablation or puncturing with fine needles and reach through to underlying, viable epidermis. Interstitial fluid from the viable epidermis or fluid from the extremity of the vascular system is then typically either sucked up, or squeezed out, from beneath the skin into the transdermal device where it is analyzed spectroscopically using systems of micro-fabricated channels and light guides.

Such systems have significant drawbacks, including the fact that the size of the holes is typically of the order of tens of microns which is sufficient to cause local irritation. this often results in inflammation, meaning that the channels typically cannot be maintained open for longer than a few hours to a few days.

Furthermore, micro-fabrication of complex systems typically requires the use of silicon substrates which are relatively inflexible, making close surface contact difficult and resulting in lateral motion between the transdermal detector and the holes through the stratum corneum. Because of the size of the transdermal holes, typically tens of microns in diameter, even a small amount of lateral motion renders such a device inoperative.

To achieve the goal of minimally invasive, continuous real-time trace transdermal sampling, analysis and delivery a system and method that overcomes these difficulties is needed.

DISCLOSURE OF INVENTION

The present invention relates to a system and method that allows trans-dermal sampling that is minimally invasive and can be used for continuous real-tome trace sampling of interstitial fluid from the viable epidermis.

In a preferred embodiment of the invention, the trans-dermal platform has a flexible substrate on which a pair of sample electrodes are joined by a resistive element. An electro-conducting enzyme anchor layer covers part of a t least one of the sample electrodes, and a protective layer may cover the entire trans-dermal platform except for the vicinity of the sample electrodes.

During manufacture, the electro-conducting layer is electrochemically activated with an anchored enzyme that modifies a target bio-molecule. For instance, if glucose is the target bio-molecule, the enzyme may be, but is not limited to, glucose oxidase.

In one of several analytic uses, the trans-dermal platform is preferably adhesively held in contact with a subjects skin. The subject's stratum corneum in then disrupted by applying a series of voltage pulses of approximately 2V lasting less than a second. The exact sequence and voltage required must be adjusted for the particular subject and the location and nature of the tissue to be disrupted. the heat and voltage drop between the sample electrodes does not remove the dead cells of the stratum corneum but severs connections between them, creating capillary openings that serve to wick the interstitial fluid from the viable epidermis up to sample electrodes and allow sufficient fluid transfer to equilibrate and dynamically maintain equilibrium with interstitial fluid in the viable tissues beneath the stratum corneum.

Any target bio-molecule in the interstitial fluid drawn into the vicinity of the electro-conducting enzyme anchor layer interacts with the anchored enzyme. This interaction may be detected by, for instance, chronoamperometric measurements made using voltages applied across the sample electrodes.

These and other advantages of the system will now be described by reference to the accompanying drawings.

BRIEF DESCRIPTION OF DRAWINGS

FIG. 2 is a schematic drawing showing the functional components of the sampling, analysis and delivery device.

FIG. 3 is a schematic top view of part of a preferred geometry of a sampling, analysis and delivery cell.

FIG. 4A is a schematic top view a preferred geometry of a sampling and analysis cell.

FIG. 4B is a schematic top view a preferred geometry of a delivery cell.

FIG. 4C is a schematic top view of an embodiment geometry a sampling, analysis, and delivery cell.

BEST MODE FOR CARRYING OUT THE INVENTION

Figure 1:
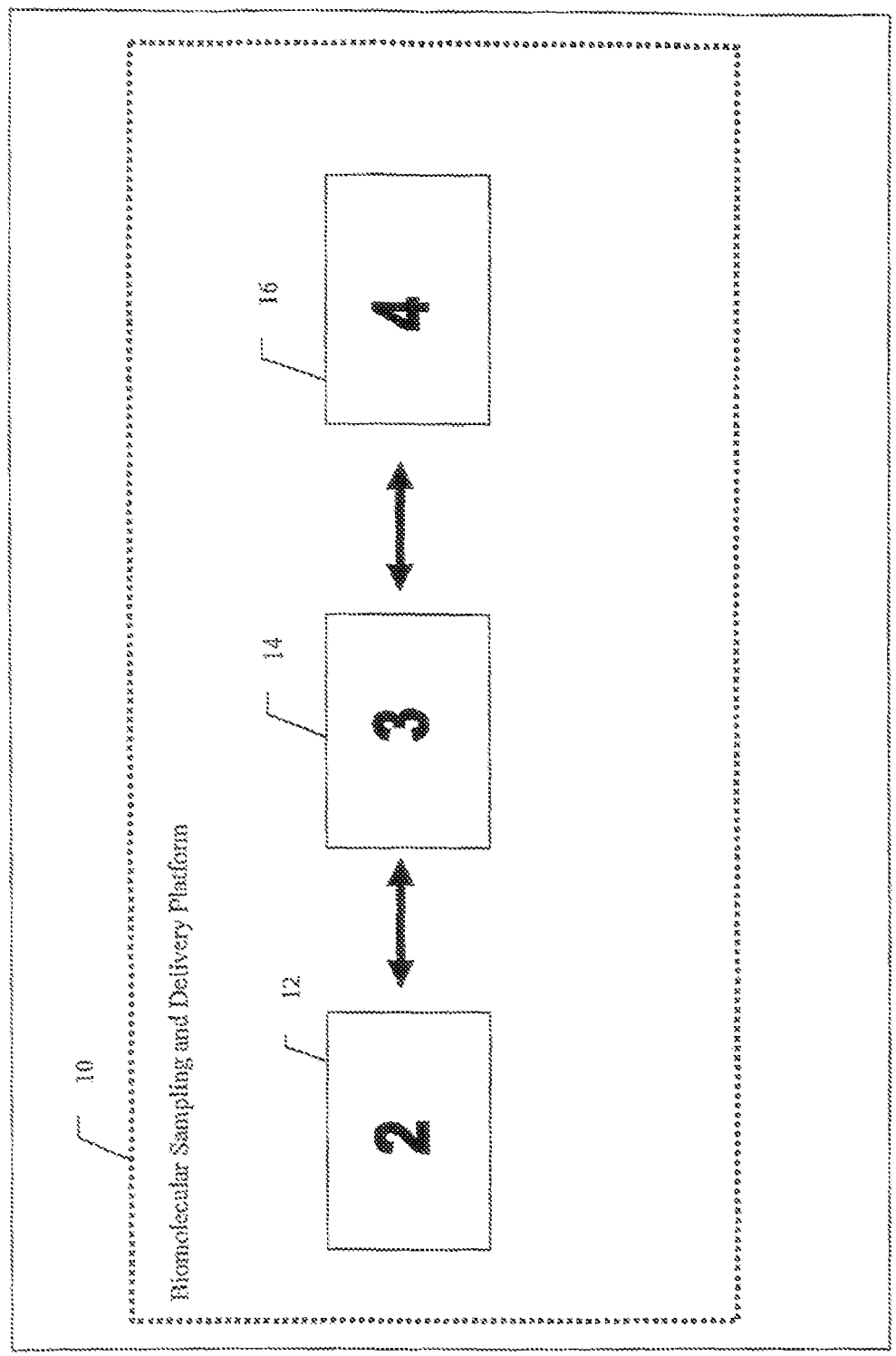
FIG. 1 is a schematic drawing showing the biomolecular sampling and delivery platform.

The present invention relates to a system and method for selective minimally intrusive sampling of biological fluids, selective electrochemical measurement of multiple bio-molecules present in the sample, and release on command of stored bio-chemicals.

In a preferred embodiment the system comprises a compliant, sterile disposable sampling, analysis and delivery device, a controlling device, and a communications device In a preferred mode of operation where biomolecules present in interstitial fluid are to be sampled transdermally, the sampling device is placed in close contact with the skin and held in position by pressure or an adhesive. A precisely determined and controlled series of electrical pulses are applied to one or several pairs of a multiplicity of selectable electrodes so as to produce heat and local electrical fields that disrupt the dead skin cells of the stratum corneum without damaging living cells immediately below them in the viable epidermis, allowing interstitial fluid to flow towards and to wet the surface of that point on the sampling device and maintain a concentration in equilibrium with that of underlying tissue for many hours until the stratum corneum reforms. At that precise position, one or more pairs of electrochemical electrodes are positioned and prepared in one of several ways so as to selectively measure one or more biochemical analytes and, or physi-chemical properties such as pH or dissolved gas. Measurements a re continuous in nature and track any time variation of these concentrations reliably until the stratum corneum repairs. The preparation of the electrodes at each point may include encapsulation to protect reactive surfaces prior to beginning desired measurement. In separate multiple encapsulations at the point of measurement, biochemicals in gas phase, dry powder or aqueous solution may be stored and released by controlled diffusion through encapsulating wall materials or through sequential controlled rupture of portions of the encapsulating wall so as to allow desired concentrations of the chemical to dissolve into the interstitial fluid and gain access to the body through the locally disrupted stratum corneum. As a analytical chemistry tool, the chemical can be chosen to react and modify the composition of the local interstitial fluid, and reaction products may be measured by the multiple electrodes. Alternatively, the encapsulated chemical sample may be a calibration standard. Separately, the selected or newly selected measuring electrodes can be used to follow continuously individual's response to the administered chemical, thus efficacy can be quantified and adapted to the individual and adverse reactions safely detected and prevented at the lowest of doses. In real time the controlling device calculates the necessary sequence of electrical signals required to perform the sampling, electrochemical analysis as well as continuous logging of the results, and chemical release. The communications device allows an external device to interrogate the controlling device so as to perform a variety of operations including identifying the system, establishing the identity of the interrogator, transmitting stored information, allowing reconfiguration of the controlling program. Reconfigurations might include opening several sampling points on the sampler surface to test for the same of multiple different analytes simultaneously, or chosing to increase, decrease or stop chemical release, or changing the frequency of sampling due to a detected stability or rapid change in measured concentrations, or adjusting the details of the pulses used to disrupt the stratum corneum. Once after potentially weeks of monitoring the electrochemical sensing points are all used-up, or encapsulations are all opened the disposable sampling, analysis and delivery device can be discarded and another one of identical or different configuration reinserted into the system.

Some similar situations to the one described in this mode of operation include:
a) monitoring for viability and functionality organs and tissues prepared and stored for surgical implantation
b) monitoring entire chemical panels for individuals, patients, or populations at risk
c) monitoring for critical care, shock, trauma and resuscitation
d) monitoring for chronic critical diseases
e) monitoring for early detection of disease
f) monitoring for response to therapeutic treatment
g) gene therapy: Scaling the individual sampling site on this device to the scale a dimension of 10 micrometers or less, the intracellular fluid of individual cells can be analyzed by disrupting the cell membrane locally, and therapeutic can be injected into the cell before releasing it from the sampler surface.

In a second mode of operation, biological fluids may have already been collected from samples of food water, air, whole blood, urine, saliva, chemical reactions or cultures. Small volumes of the biological fluids may be applied to the surface of the sampling device either statically or by means of a continuous flow across the surface. The controller is configured to open one or several sensing sites and begin monitoring specific concentrations. For example blood draws can be analyzed immediately at the point of care, or air and water samples can be monitored continuously for chemical- and biological contaminant-free purity. Samplers can be replaced as used-up or as new contaminant threats are identified enabling a flexible reconfigurable monitoring.

Some similar situations to the one described in this mode of operation include:
a) monitoring cell culture viability and metabolism
b) monitoring precipitates, distillates, filtered powders.

System Components

In a preferred embodiment, the system consists of three functional devices. Referring to the lettered features of the photographs in FIG. 1 below, we see A) Flexible disposable micro fluidic electro-chemical chip with multiple electrochemical sensor cells, C) and D) a controller device comprising a flexible cable and connector, together with a wireless control and messaging unit, and thirdly a communicating device or interfaced remote Wireless computer.

The sampling device may be a flexible patch-like chip with a multilayer polymeric metal laminate structure and may be fabricated using SU-8 as a structural layer, a Teflon-AF release layer, polymethylmethacrylate (PMMA), polypyrrole (PPy) and glucose oxidase (GOD). For brevity we shall describe a particular version of the device in which for clarity the encapsulation and protective membrane rupture features are absent, and in which we have chosen to combine the electrodes used for disruption of the stratum corneaum with the sensing and reference electrochemical electrodes. The sampling, analysis and chemical delivery device fabrication process uses SU8 as a principal structural material consisting of five steps. This process is a subset of an earlier technology developed for the polymer material PDMS. The first step was the deposition of a Teflon release layer on a glass substrate, which allowed the multi-layered multi polymeric devices to be removed easily from the glass after fabrication. A thin layer of SU8 was formed by spin coating and acted as a base layer (10μ) for the rest of the device and provided adhesion to the Teflon. The third step in the fabrication process consisted of spin coating a thick (150μ) SU8 layer. This thick layer provided the structural support for the device. Chromium/gold electrode/heater metallization (0.5μ) was sputtered deposited and patterned on top of the thick SU8 (150μ) layer. 10μ PMMA was then spun coated as a protective layer for the selective deposition of PPy and enzyme. In order to prevent electrode pads getting covered by PMMA, scotch tape was applied on the electrode pads prior to PMMA spin was removed before PMMA baking process. PMMA layer was further selectively plasma etched in such a way that any one of the electrodes was exposed and the other electrode was covered. The metals were patterned using positive photo-resist and wet-chemical etching. Before the sputter deposition, a plasma surface treatment was employed to improve the adhesion between the SU8 and the metal layers. Releasing the device from the glass substrate using a razor blade was the next step. The release layer was formed by spin coating a solution of amorphous fluoropolymers diluted with perfluorinated solvent.

Glucose oxidase (GOD), the current enzyme prototype, was adsorbed electrochemically onto a polypyrrole (PPy) layer using a potentiostat together with an electrolyte solution consisting of 0.1 M, each, of PPy and KCl at 0.8 V for 2 minutes. 0.1 M Ferricyanide and 8001 units/ml of GOD (18 .mu.l GOD and 48 .mu.l K3FeCN6 in 10 ml phosphate buffer solution) were further added in the electrolyte solution for the deposition of GOD. Selective deposition of Ppy+GOD was then done on one of the exposed electrodes of the SAMPLING, ANALYSIS AND CHEMICAL DELIVERY DEVICE cell (FIGS. 4A-4C). Chronoamperometric dose responses were recorded and the results revealed that the sensor had a good linearity from 0 to 10 mM glucose with the sensitivity of 2.9 mA/mM. For our lactate sensor chips we use the same process except we substitute lactate oxidase for the GOD.

Control Electronics

Again for simplicity we discuss a prototype realization of the control functions in a simplified system.

We modified the design of sampling, analysis and chemical delivery devices to make them compatible with zero-insertion force (ZIF) connectors. Chip thicknesses were adjusted to be 150 μm±10 μm for optimal insertion reproducibility and the connector pad pin-outs were drawn to meet with the 300-pitch staggered connector positions. Most important is the ability to make "bottom" chip contacts allowing a flat connector and chip surface that can be pressed to the body of the subject. That is, there is no step in level at the connector body that prevents a good flat contact with the skin. The body of the connector is 1.8 mm high in a surface mountable dual in-line package and is equipped with a ZIF slider mechanism that locks the chip into place once correctly inserted. We have seen that this allows us to change sampling, analysis and chemical delivery device sensor chips reproducibly in a minute, yet be sturdy enough to accept multiple insertions and to resist forces that would withdraw the chip from the socket due to the normal movement of the animal under experimental study. The part is made in different widths corresponding to a range of 17 to 91 pin contacts. We have used the ones for 31 and 61 pins in our development work. The connector photographed in FIGS. 1, 7D, 8G and 8H is the 61 pin version soldered to a wire cable. We have also used in with flexible multi-conductor kapton tapes as shown in FIG.1C. In the integrated device shown in FIG. 1F this connector is rigidly connected to the body of the control electronics package. The connector is available in both tape and reel-to-reel packages for economic automated assembly and manufacture.

The electronics consists of two parts. The first is a computer-interfaced wireless data collection system that is capable of addressing up to 64 remote sensor nodes managing the identification of each one as well as interrogating each one for the contents of its memory buffers. The second part is the sensor node. It is made up of five functional parts: RF communication (with unique identification), a microprocessor controller, a multiplexer, analog circuit sources and A/D converters, and multiple sensor input. The modifications made by Holeman concern principally programming the microprocessor, and adapting the analog circuits, multiplexer and input lines to our device. The details of this electrical engineering will be given elsewhere. Of importance is that the range of communication is about 300 m to allow communication between a command center and members of a platoon. Each soldier can be monitored individually for glucose and lactate concentrations. If the soldier is healthy, an individual rested baseline can be measured and stored. As the soldier exerts himself the blood glucose and lactate levels can be monitored. Extreme exerting can be seen in hypoglycemia and elevated lactate levels. This physiological state affects the soldier's ability to perform in battle or subsequent situations of high-exertion. If the soldier suffers a casualty, the monitors can be activated to measure quasi-continuously as shown in the studies below, and the micro system behaves as a critical care and triage instrument.

Trace Detection by Using Nanomaterials on the Sensing Electrode

Disruption of barrier tissues is different irons prior art in which processes such as ablation and position are typically used. Ablation refers to the removal of certain targeted cells for example is the stratum corneum stack of mammalian skin. Barrier cells are often not living cells, and are sometime scaly and flattened from their living shapes, are closely and conformally packed adhering one to another by chemical bonds between the biomoleculars constituting cell walls. The process of disruption refers to the process by which the bonds between fee packed barrier cells are gradually broken, allowing narrow capillary openings to form between cells. The cells themselves mostly remain intact. At one point as the capillary size increases there are conductive paths through which interstitial fluid can be drawn, to the surface. Our observation is that the rate and nature of flow is independent of, for example, basal metabolic blood pressure and there is no internal pressure head forcing ISF outwards. ISF flows can be enhanced with special hydrophyllic surface treatments of the sampling points on the sampling device as well as in capillary structures or tiny enclosures patterned into the surface of the sampling device.

Our unique technique for reliable disruption of barrier tissues requires a particular sequence and combinations of pulses of electrical energy on the individually addressed sampling electrodes. In particular for human forearm skin we have used one or multiple conducting thin film resistors between the sampling electrodes. For multiple resistors the values of the resistances are chosen to cascade from a high (eg, 200 Ohm) to medium to low resistance (50 Ohm). The size of each resistor is comparable to that of the barrier cell to be dislodged from its neighbors. For 50 micron stratum corneum cells this means that the gap between electrodes is less than 100 microns. Electrical voltage steps from 0 to 2 V are applied to the electrodes in short bursts of less than one second, typically with 0.2 V increases in each pulse. This first applies a moderate electric field of up to 4 MV/m. Then by 2.2V the temperature of the least resistive element reaches 140 C very briefly, and the resistor opens. Opening is determined by the precise fabrication materials, dimensions and sequences of the resistor and the underlying sampling device material (often a low melting temperature polymer film such as poly ethylenes or methacrylates). By material deformation the conductive trace breaks. Heat profile measurements show that the temperature falls to less than 80 C across a 50 micron thick stratum corneum. If there is only one resistor, the electrode goes into open circuit, yet still an electric field can be applied in pulses between the electrodes. For multiple resistors, one can continue the voltage steps until all resistors break to open circuit. The electrodes can now be left alone to allow for electrochemical measurements between sensing and reference electrodes.

Of note is that one realization is to use the disrupting electrodes themselves for the electrochemical measurements. When possible, benefits of this particular realization are compact economical fabrication, higher packing densities, simplification of connection and control circuitry.

To understand the inventive concepts of the present invention it is users! to consider the accompanying drawings in which, as Sir as possible, like numbers represent like elements.

FIG. 1 is a schematic drawing showing the biomolecular sampling and delivery platform 10. The platform 10 comprised three cooperating devices, the sampling, analysis, and delivery chip 12, the control electronics 14, and the wireless interface 16 that allows transmission of data to remote loggers or controllers.

FIG. 2 is a schematic drawing showing the functional components of the sampling, analysis and delivery chip 12. The sampling, analysis and delivery chip 12 comprises the sampling analysis and delivery cell area 18, the electrical contact pads to controller's socket 20 and the electrically conductive paths 22 that connect the chips 12 to the contact pads 20. The chips 12 are located in an area 24 placed in contact with tissue or sample to be analyzed. The chip 12 optionally includes an electrical chip identification area 26.

FIG. 3 is a schematic top view of part of a preferred geometry of a sampling, analysis and delivery cell 12, that may be one of many on the sampling, analysis and delivery device 10. In this geometry both sampling and analysis devices are exposed on the surface of the compliant device. A buried encapsulation 28 containing material for delivery is shown in outline.

Electrically conductive paths 30 are covered by thin insulating layer and form part of a selective working electrode 32 and a reference electrode 34.

Exposed electrically resistive element portions 36 join the exposed section of electrically conductive paths 38 of a second conductive path.

FIG. 4A is a schematic top view a preferred geometry of a sampling and analysis cell. In this layout, the selective working electrode 32 and the reference electrode 34 are joined by the exposed section of electrically conductive paths 38 of a second conductive path so that the disruption of the stratum corneum and the chronoamperometric or other electrical analytical measurements can be made by the same electrodes.

FIG. 4B is a schematic top view a preferred geometry of a delivery cell. In this layout the buried encapsulation 28 containing material for deliver is located behind a pair of exposed sections 38 of electrically conducting paths joined by an exposed resistive element portion of the conduction path. In this way disruption of the stratum corneum may used to provide delivery of the material in the buried encapsulation 28.

FIG. 4C shows a top view schematic of one part of one particular geometry of one sampling, analysis and delivery cell of many on the sampling, analysis and delivery device. In this geometry both sampling and analysis devices are exposed on the surface of the compliant device and the electrodes are located at the exposed portions of the electrically conductive paths, resulting in fewer conductive paths, and requiring increased control functionality.

Figure 5:
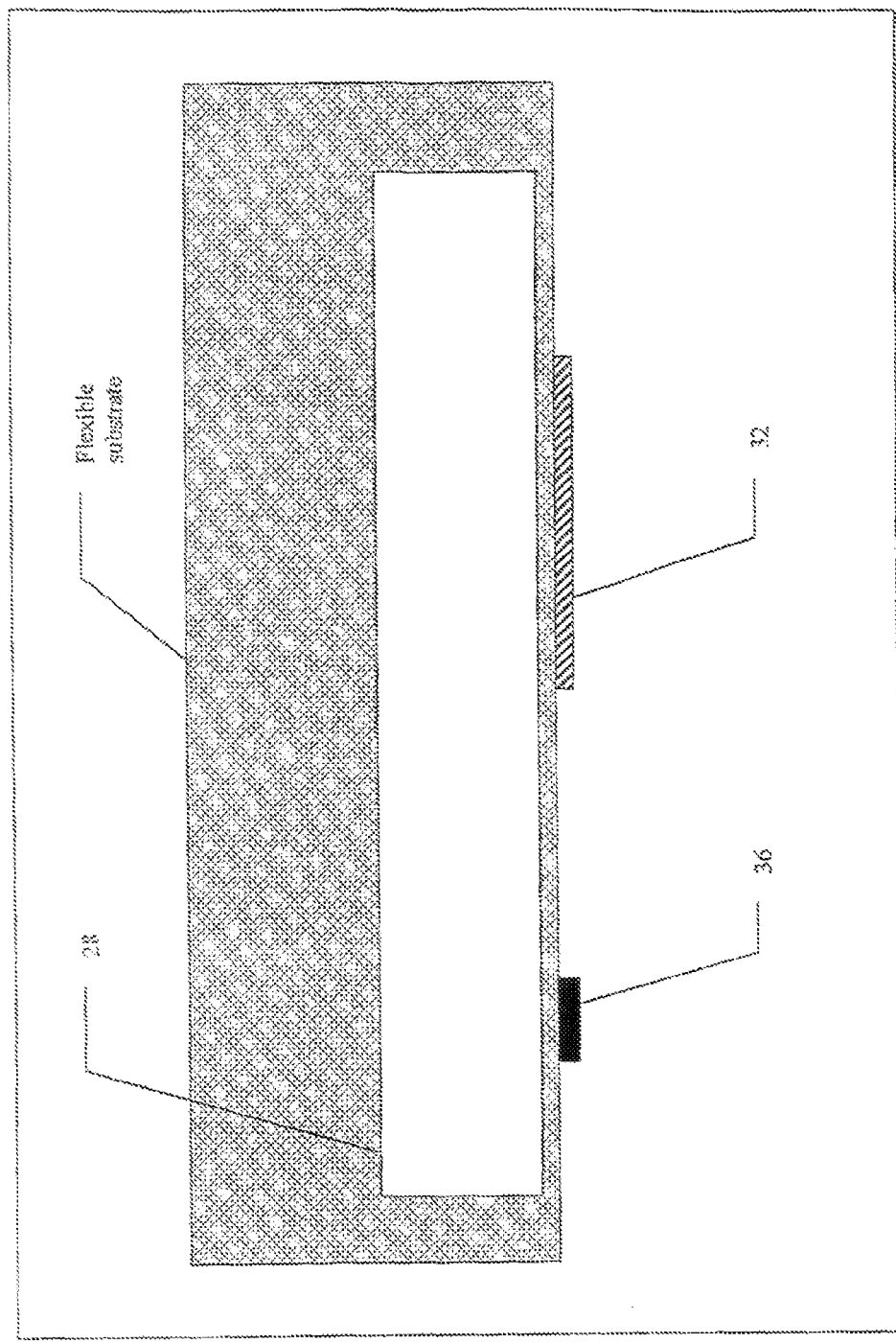
FIG. 5 shows a cross section along A-B of the embodiment of FIG. 3.

FIG. 5 shows a cross section along A-B of the embodiment of FIG. 3.

The cross-section shows the resistive element 36 in proximity to an analysis electrode feat may be a selective working electrode 32 on a portion of the flexible substrate 40.

Figure 6:
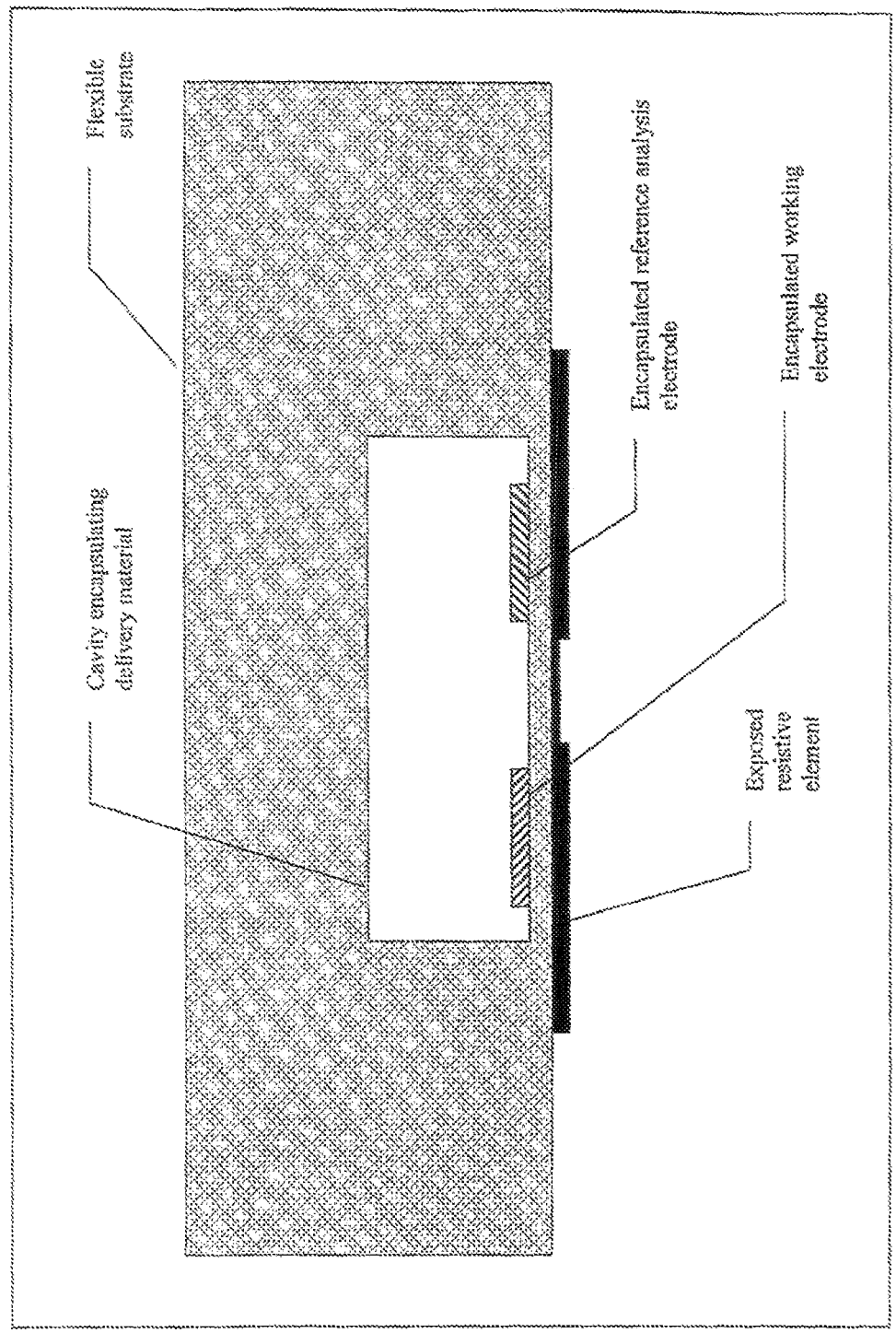
FIG. 6 is a schematic cross section of a variation of the design depicted in FIG. 3.

FIG. 6 is a schematic cross section of a variation of the design depicted in FIG. 3 in which the analysis electrodes 32 and 34 are encapsulated within a cavity in the substrate 40 and are on a thin membrane of substrate material at the point of sampling. The cavity 28 may be filled with material to be delivered to the sampling site, or may be empty.

Figure 7:
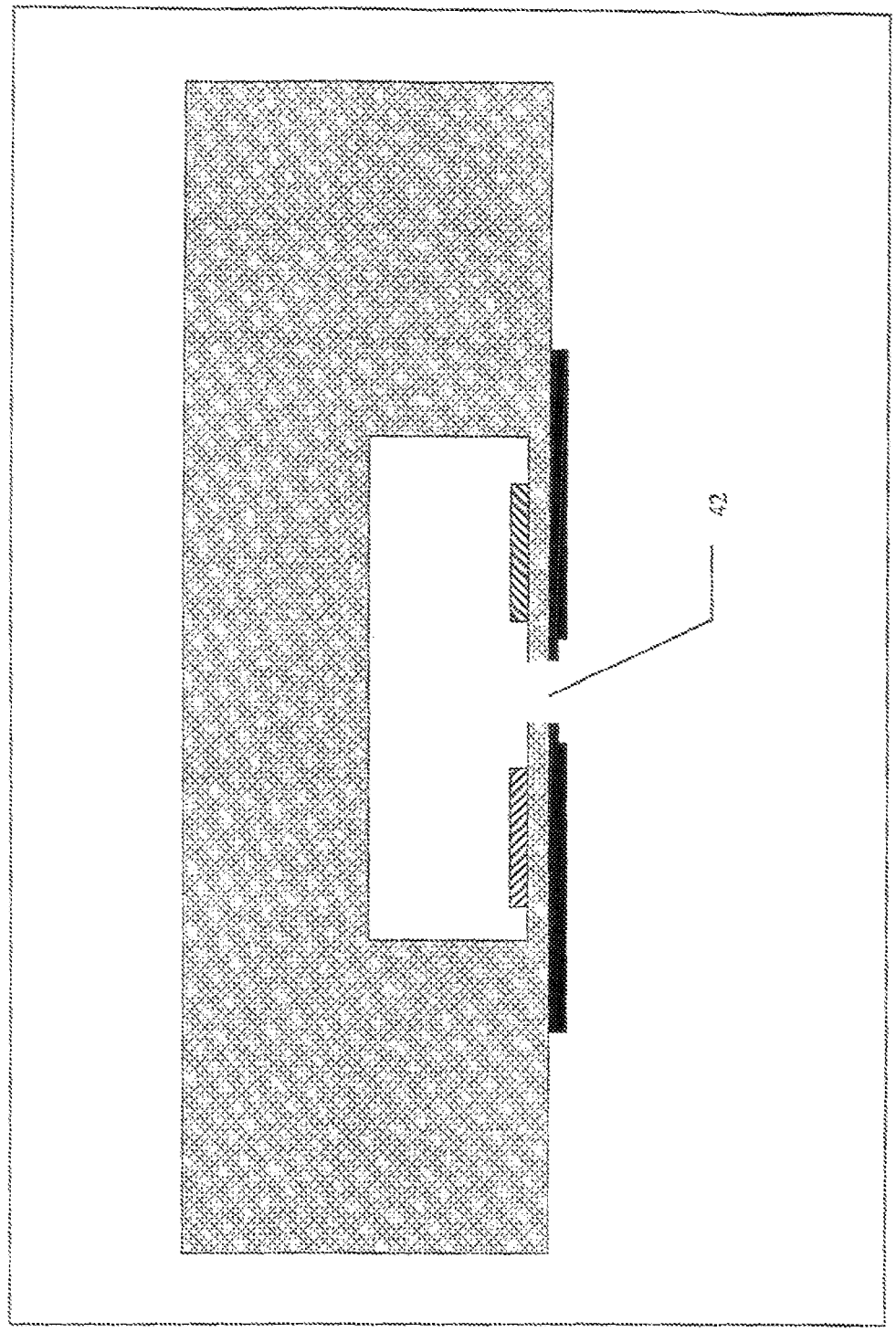
FIG. 7 shows the same cross section as FIG. 6 in which a breach 42 in the thin membrane of substrate.
Figure 8:
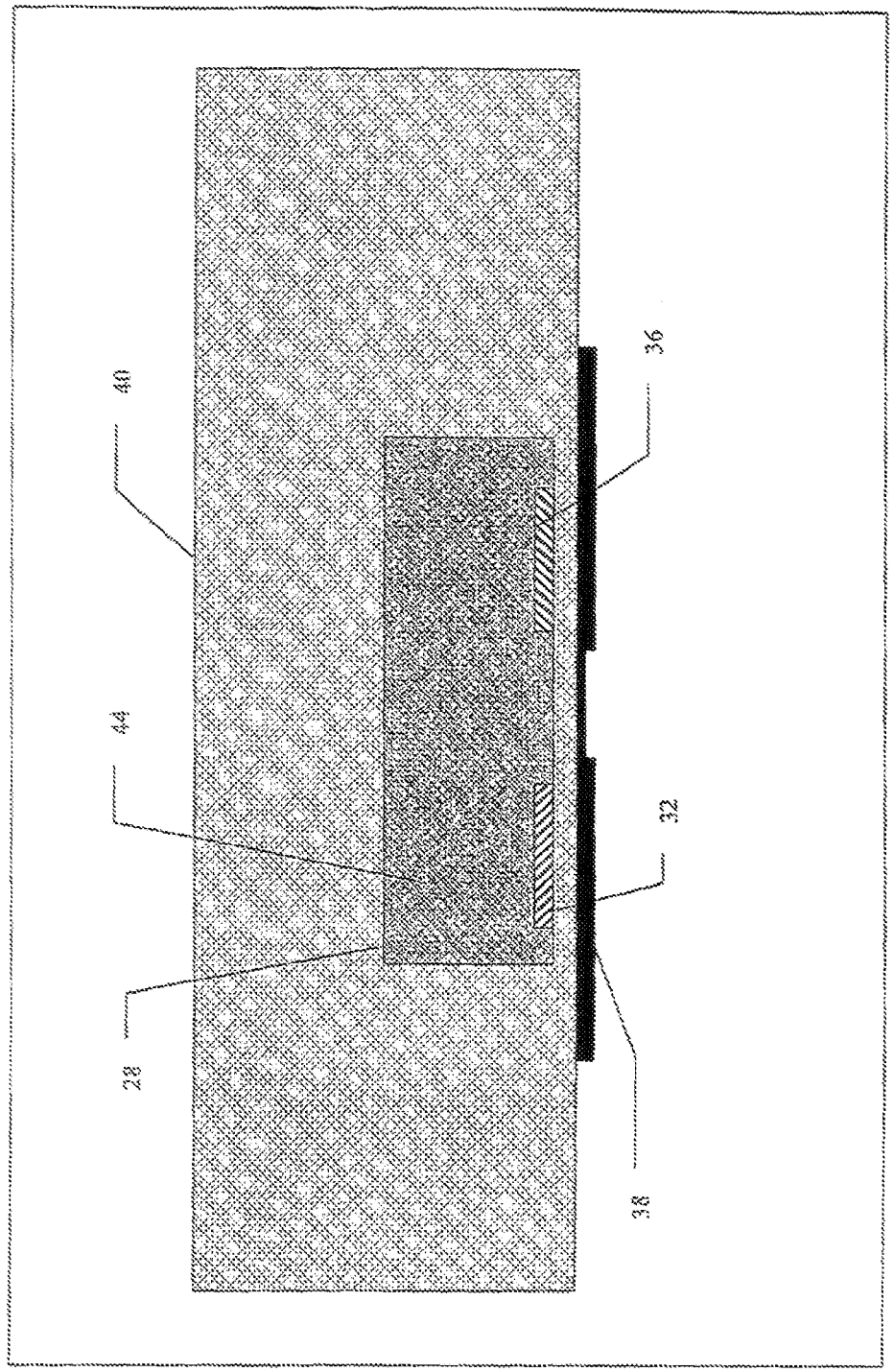
FIG. 8 shows the cross section of FIG. 6 with the cavity filled with material for delivery at the sample site.

FIG. 7 shows the same cross section as FIG. 6 is which a breach 42 in the thin membrane of substrate. The breach 42 is caused by the actuation of the resistive element results in exposure of the electrodes to sample material, allowing delivery of any encapsulated delivery material to the sampling site FIG. 8 shows the cross section of FIG. 6 with the cavity 28 filled with material 44 for delivery at the sample site. These working electrodes 32 and 36 may be configured to select for the concentration of the delivery material 44 and hence gauge how much of the material has left the cavity and has been delivered to the sampling site.

Figure 9:
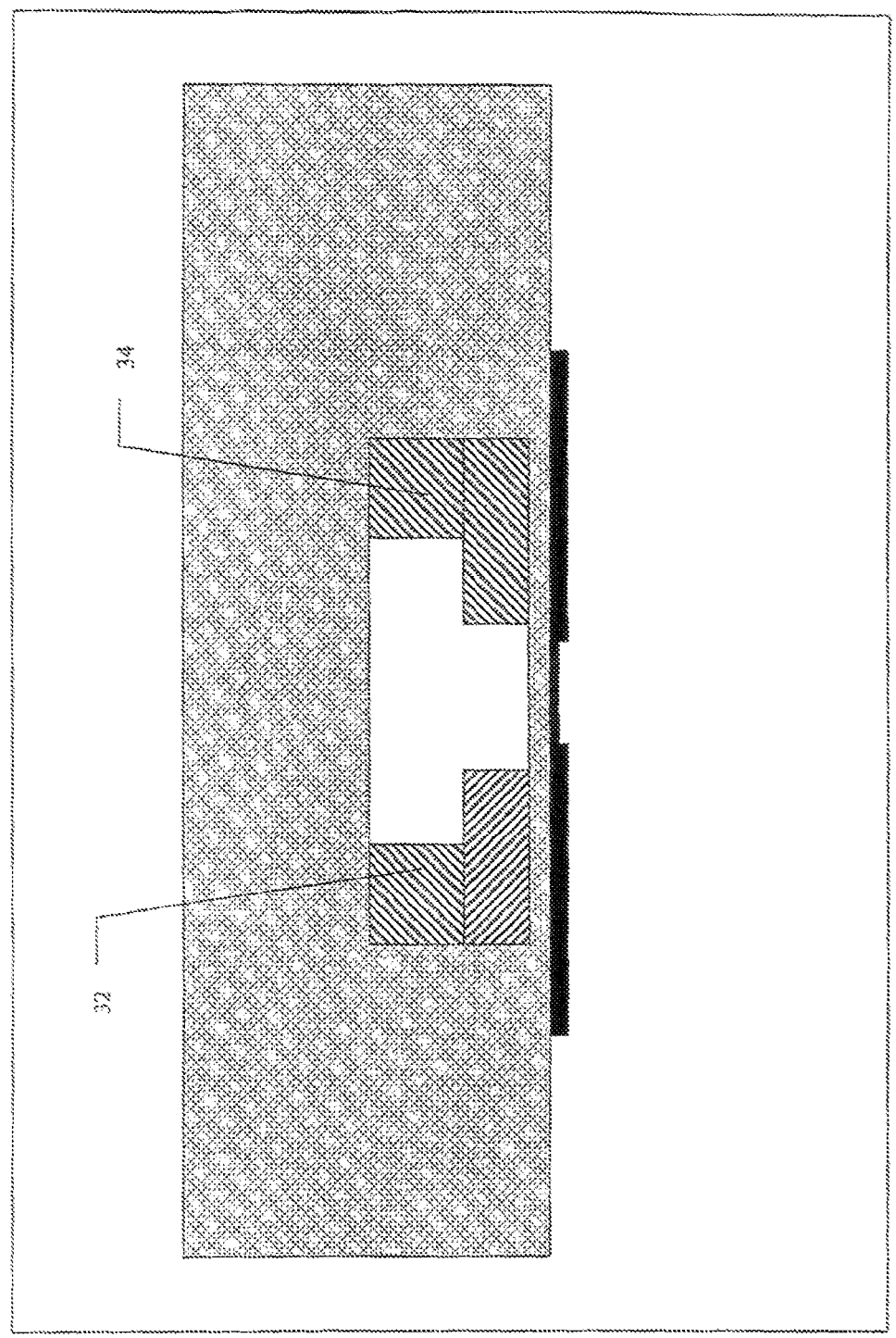
FIG. 9 shows the cross section of FIG. 6 in which the effective surface areas of the analysis electrodes 32 and 36 is increased.

FIG. 9 shows the cross section of FIG. 6 in which the effective surface areas of the analysis electrodes 32 and 36 is increased achieving a corresponding increase in electrical signal and a lessening of the signal to noise ratio. Increase in the area can be achieved both by covering additional area on the walls of the cavity as well as by using a protected spongy porous electrode material.

Figure 10:
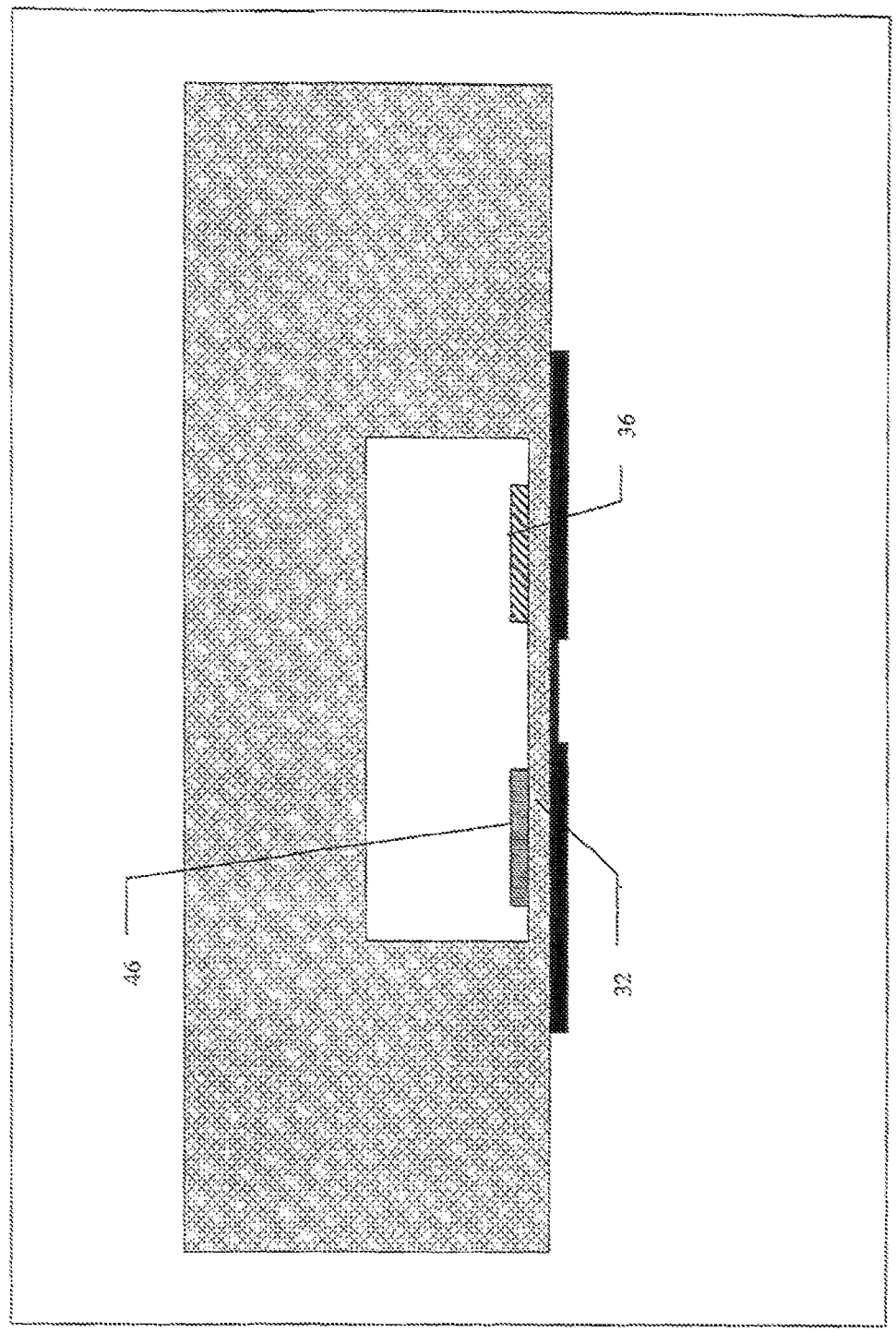
FIG. 10 shows the cross section of FIG. 6 in which the effective surface areas of the analysis electrodes is increased.

FIG. 10 shows the cross section of FIG. 6 in which the effective surface areas of the analysis electrodes 32 and 34 is increased achieving a corresponding increase in electrical signal and a lessening of the signal to noise ratio. Increase in the area can be achieved by covering the working electrode 32 surface with a protected dense nanomaterial 46 prepared with the necessary selective chemistries.

Figure 11:
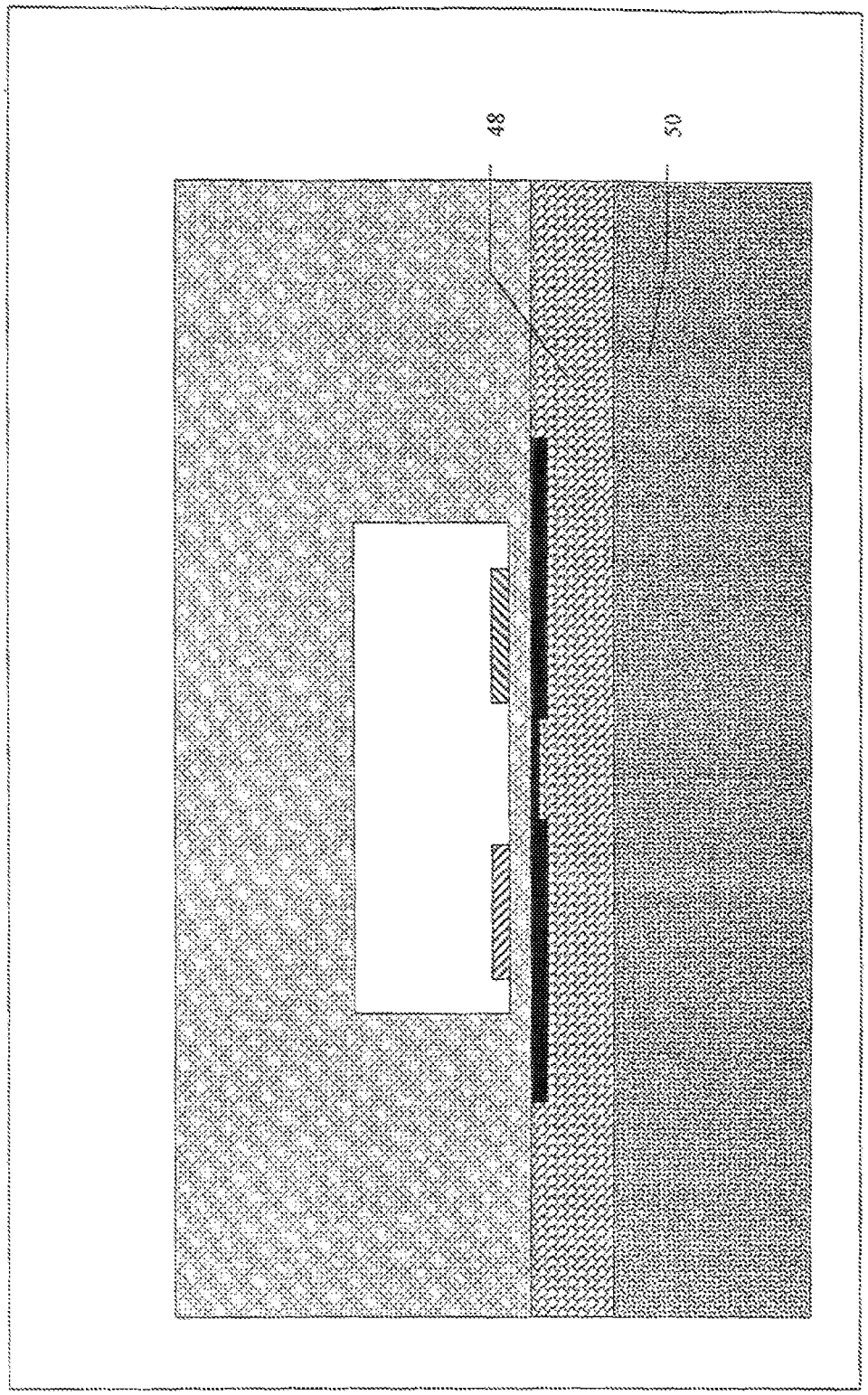
FIG. 11 shows the cell of FIG. 6 in contact with tissue such as skin which is simplified to show schematically the scaly stratum corneum and the viable epidermal tissue.

FIG. 11 shows the cell of FIG. 6 in contact with tissue such as skin which is simplified to show schematically the scaly stratum corneum 48 and the viable epidermal tissue 50 below in which is located interstitial fluid.

Figure 12:
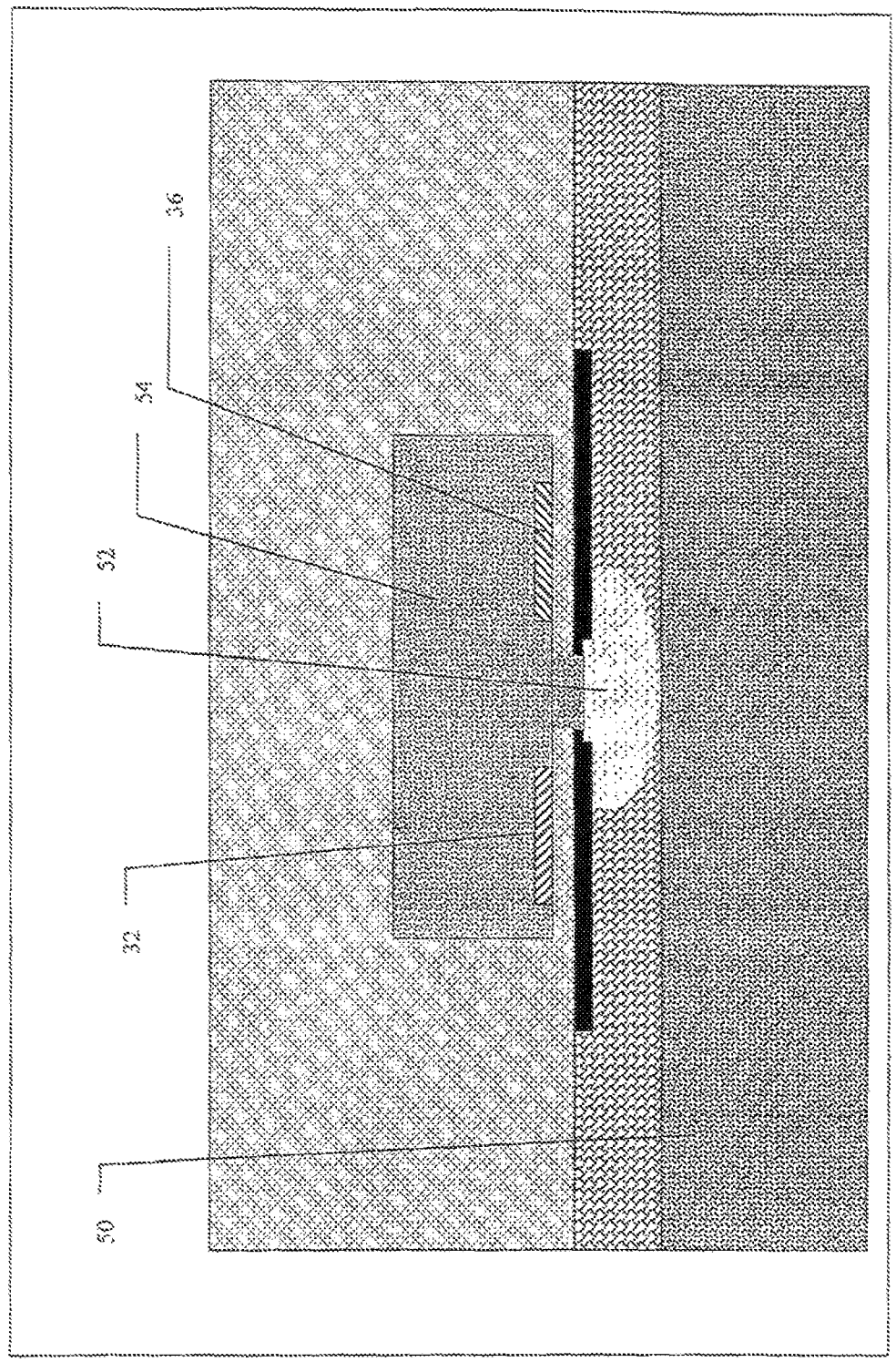
FIG. 12 is a schematic drawing showing the cell of FIG. 11 after disruption of the barrier tissue.

FIG. 12 is a schematic drawing showing the cell of FIG. 11 after disruption of the barrier tissue in region 52. A percolating fluid path is established allowing the interstitial fluid 54 from the viable epidermal tissue 50 to flow by capillary force to and wet the sampling site. The interstitial fluid 54 wetting the electrodes may be analyzed by the selective electrodes 32 and 34.

Figure 13:
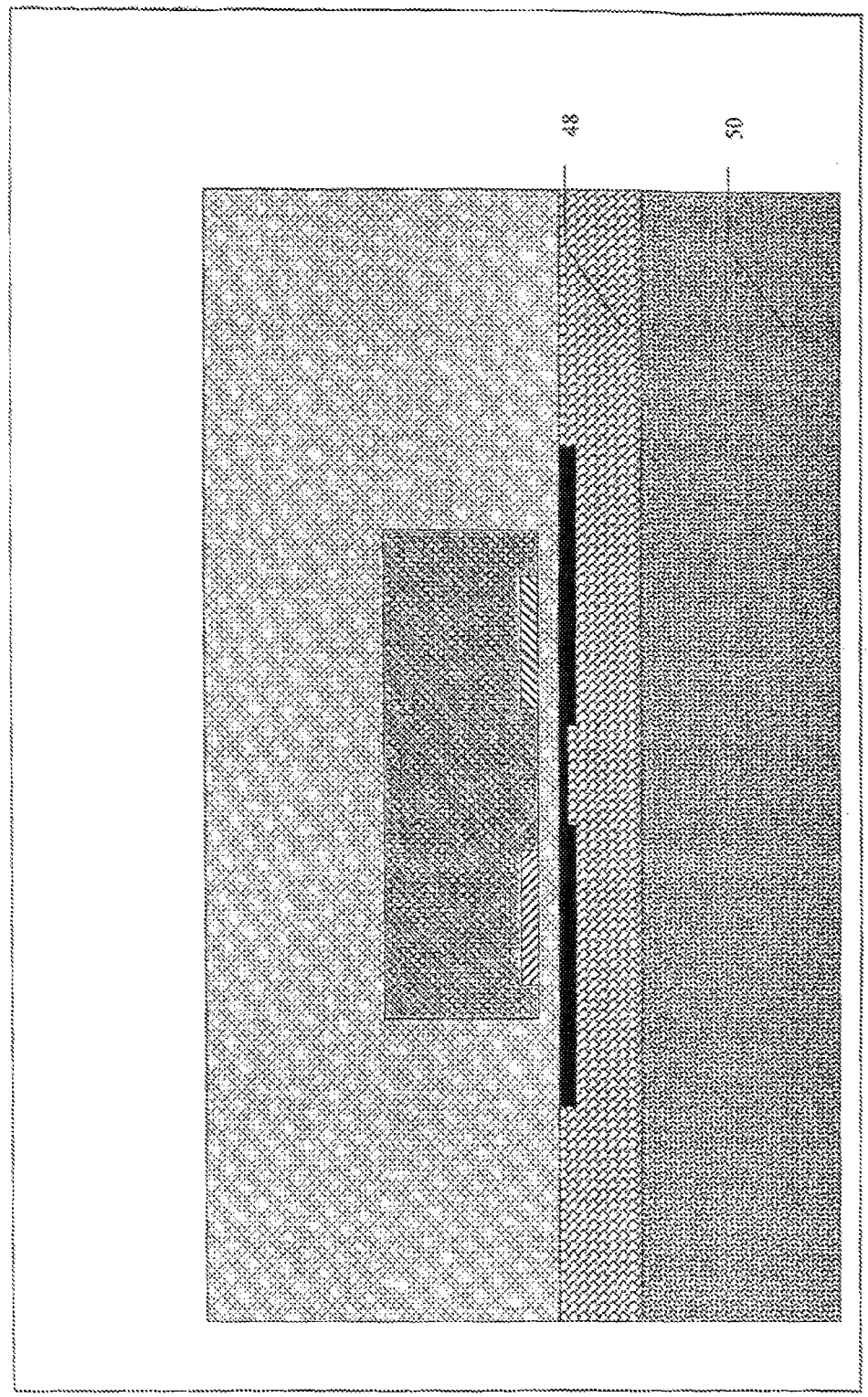
FIG. 13 shows the cell of FIG. 8 in contact with tissue.

FIG. 13 shows the cell of FIG. 8 in contact with tissue such as skin which is simplified to show schematically the scaly stratum corneum 48 and the viable epidermal tissue 50 below in which is located interstitial fluid.

Figure 14:
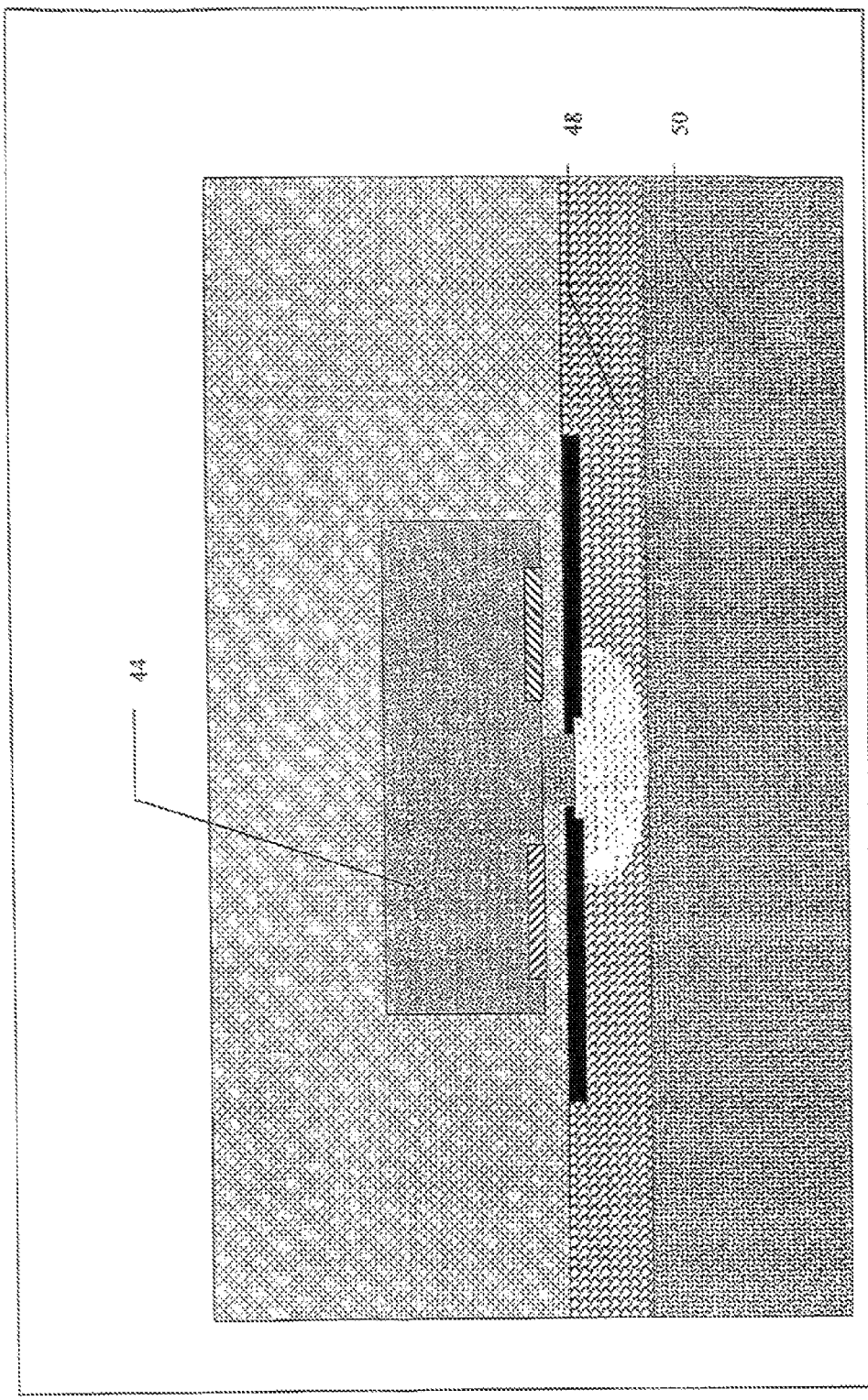
FIG. 14 shows a schematic view of the cell of FIG. 11 after disruption of the barrier tissue.

FIG. 14 shows a schematic view of the cell of FIG. 11 after disruption of the barrier tissue. A percolating fluid path is established allowing the interstitial fluid 54 to flow by capillary force to and wet the sampling site. The delivery material 44 mixes or dissolves in the interstitial fluid end due to the resulting high concentration gradient diffuses backward through the disrupted stratum corneum 48 to the viable tissues 50 and thence to the rest of the body.

Figure 15:
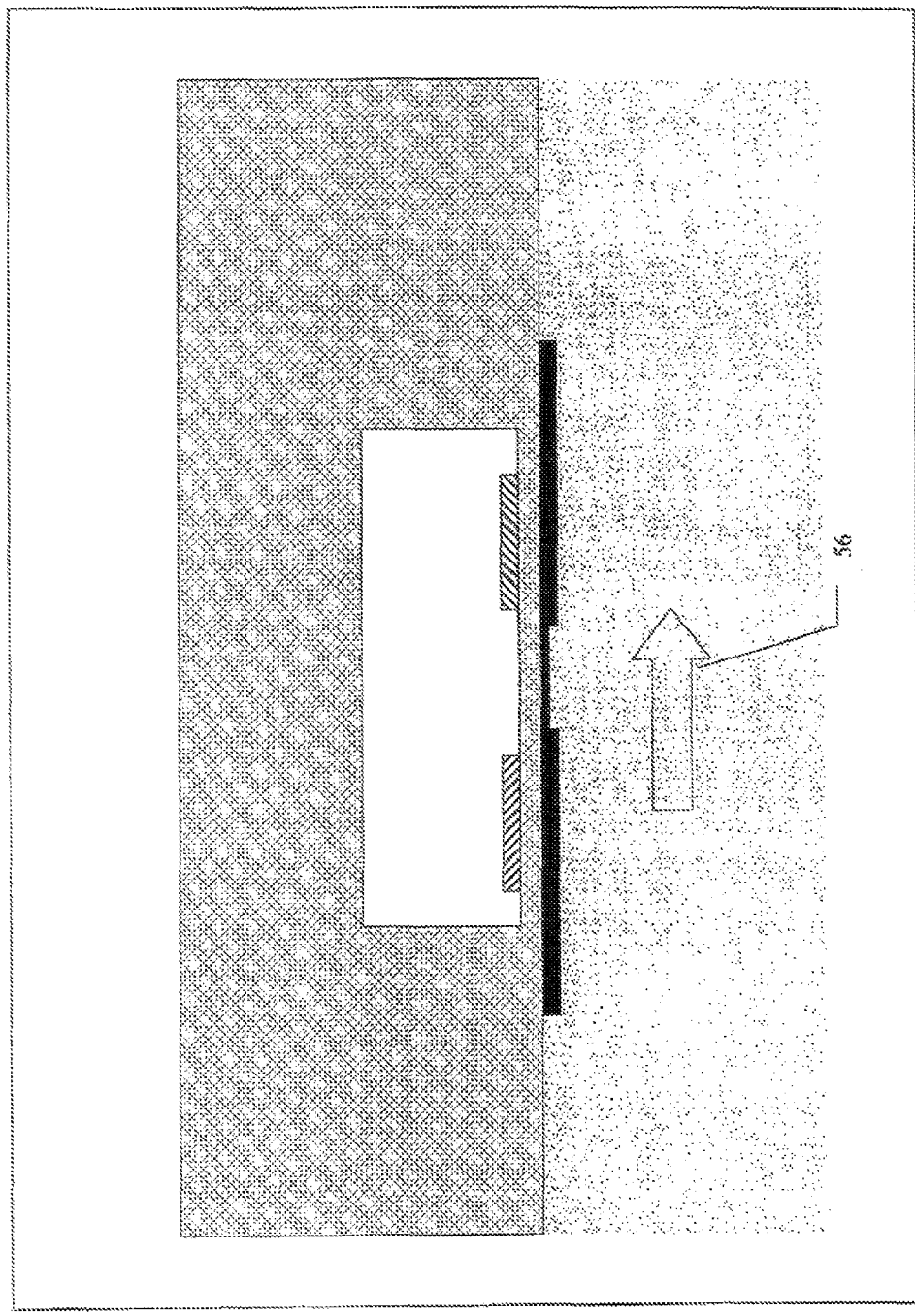
FIG. 15 shows the cell used for sampling fluids.
Figure 16:
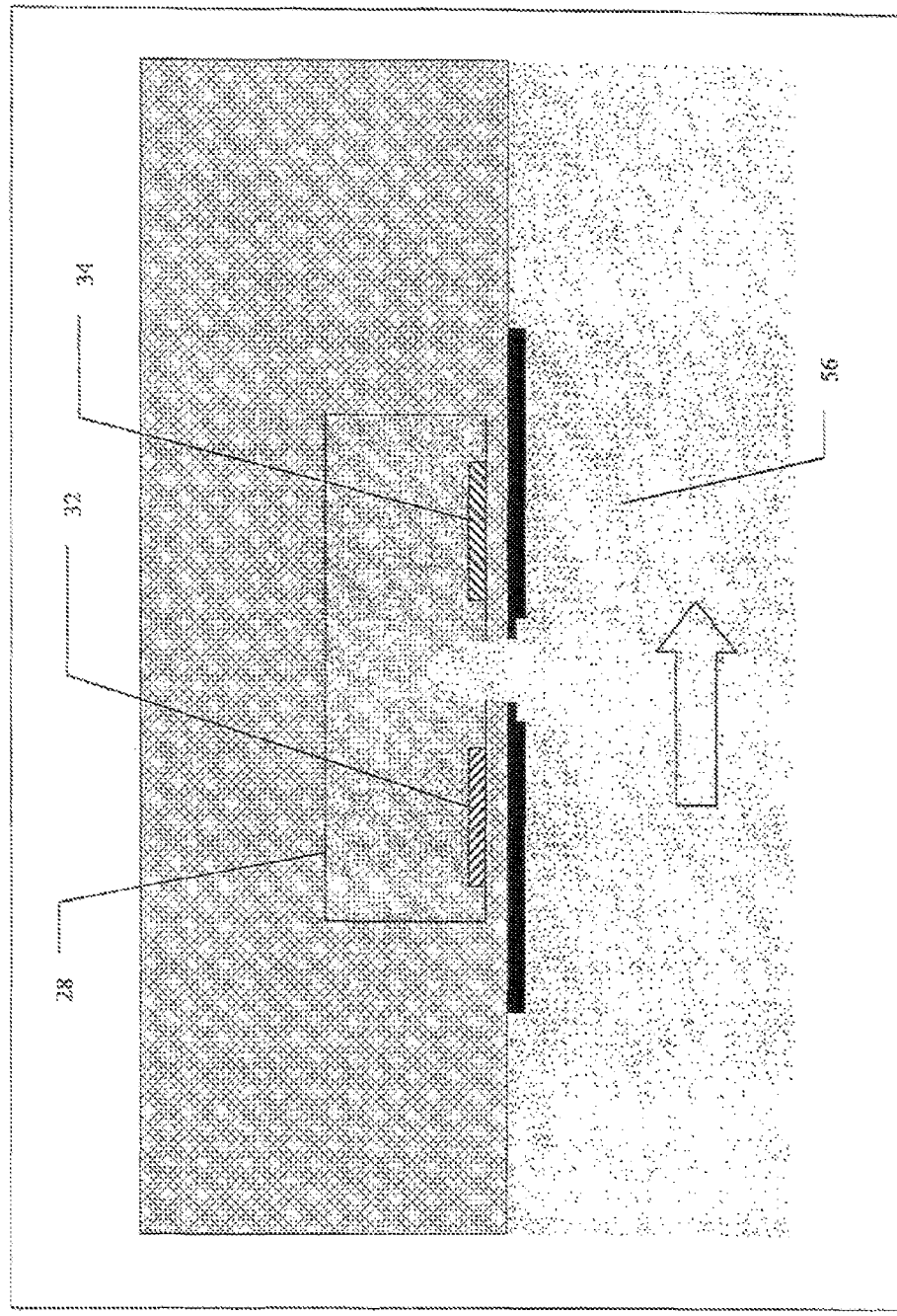
FIG. 16 showing the cell of FIG. 15 which has opened to allow fluid to enter the cavity where the analysis electrodes are located.

FIG. 15 shows the cell used for sampling fluids. The cell of FIG. 6 in contact with stagnant or flowing field 56 to be analyzed FIG. 16 shows the cell of FIG. 15 which has opened to allow fluid to enter the cavity 28 where the analysis electrodes 32 and 34 are located.

Figure 17:
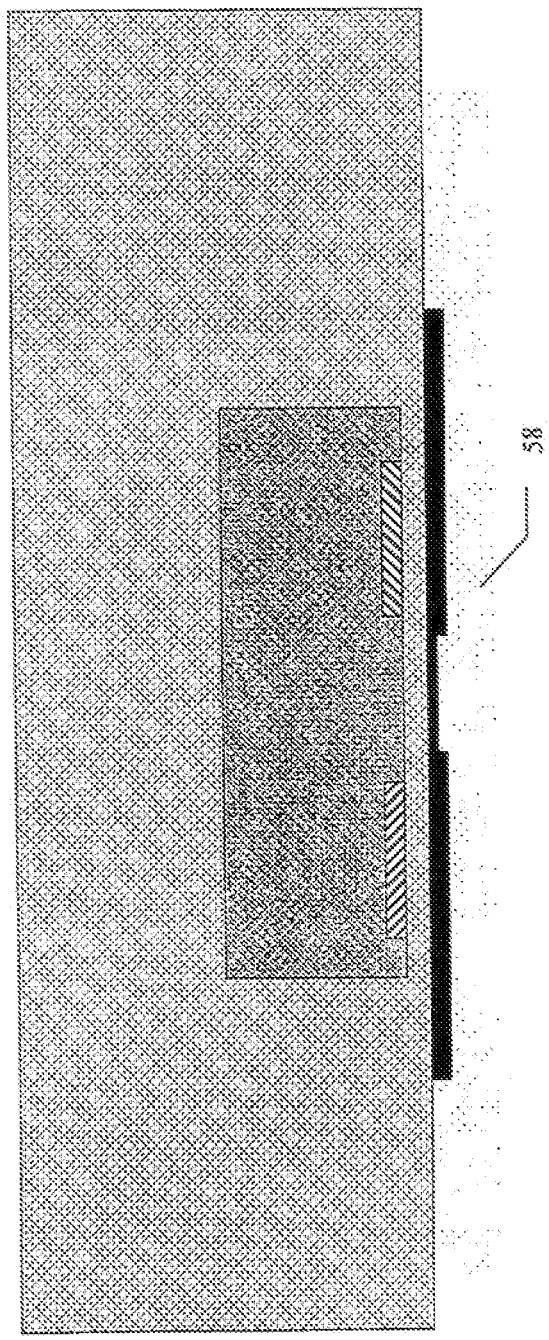
FIG. 17 shows the cells used for sampling solids or powders.

FIG. 17 shows the cells used for sampling solids or powders. The cell of FIG. 8 onto which the dry sample 58 to be analyzed has been applied or collected.

Figure 18:
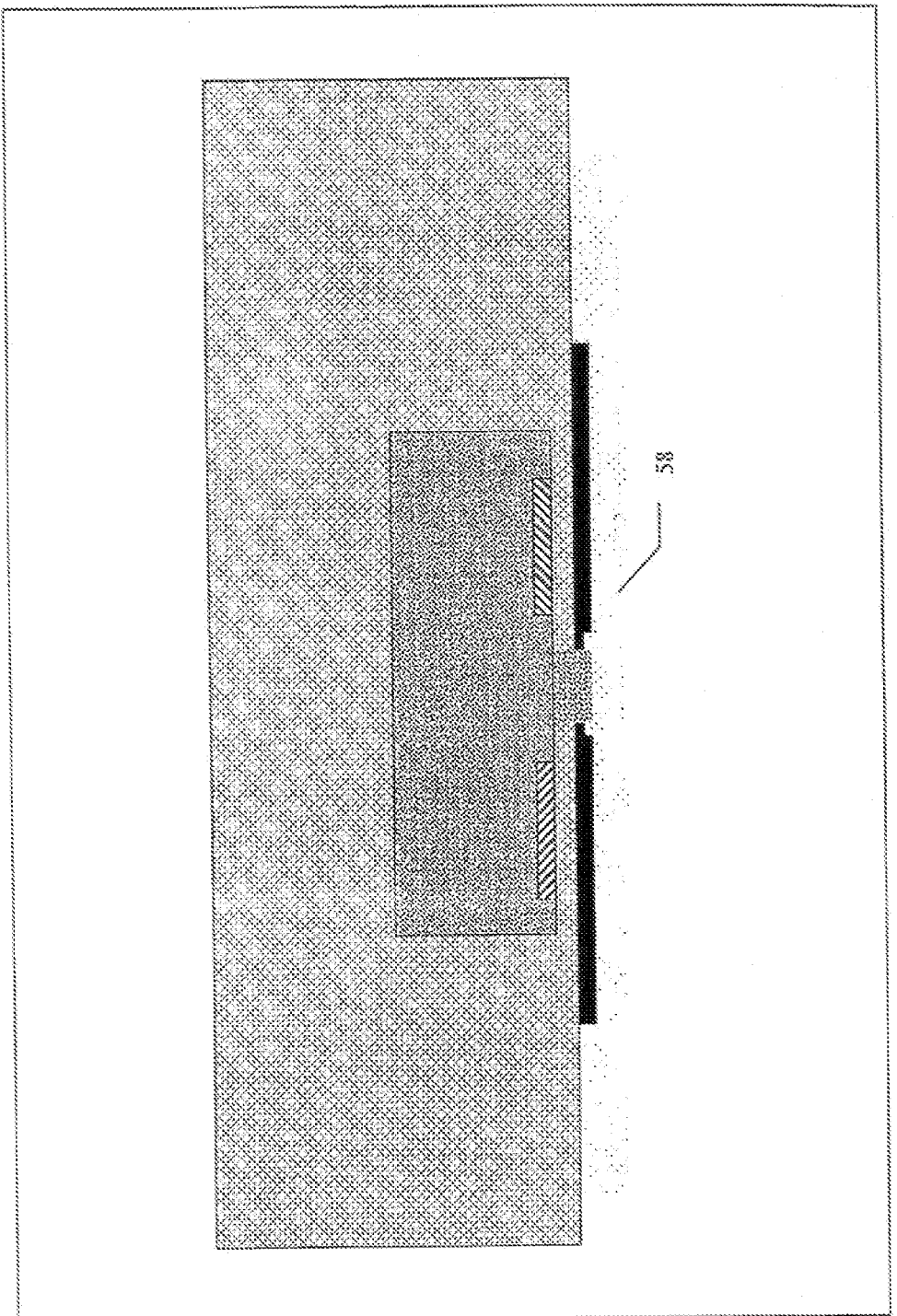
FIG. 18 shows the cell of FIG. 17 which has opened to allow contained fluid to wet and dissolve the dry sample enabling a concentration to be present at the analysis electrodes.

FIG. 18 shows the cell of FIG. 17 which has opened to allow contained fluid to wet and dissolve the dry sample 58 enabling a concentration to be present at the analysis electrodes.

Figure 19:
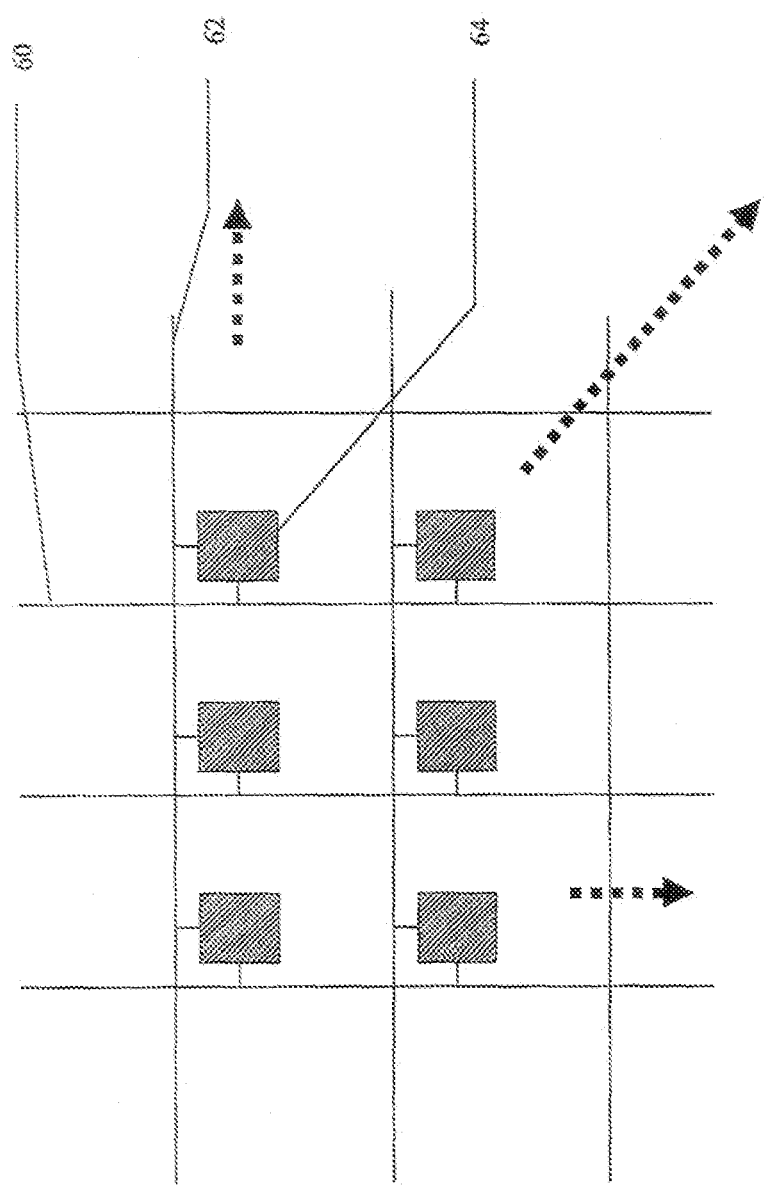
FIG. 19 illustrates an embodiment matrix of cell elements together with the row and column address lines.

FIG. 19 shows a random addressing of cell elements using row and column addressing. The address method comprises column address conductive paths 60, Row address conductive paths 62 and individually addressed sample, analysis and delivery cells 64.

This method is used instead of a parallel addressing in which each cell has its own conductive paths connecting to the controller as shown in FIG. 2. For example 1024 calls organized in a matrix of 32 rows and 32 columns can be addressed sequentially by a 64-bit connector to the controller of which 32 connections are for the row address and 32 are for the column address. To perform simultaneous sampling and analyses, the controller must continually switch between sample analysis and delivery cells.

Figure 20:
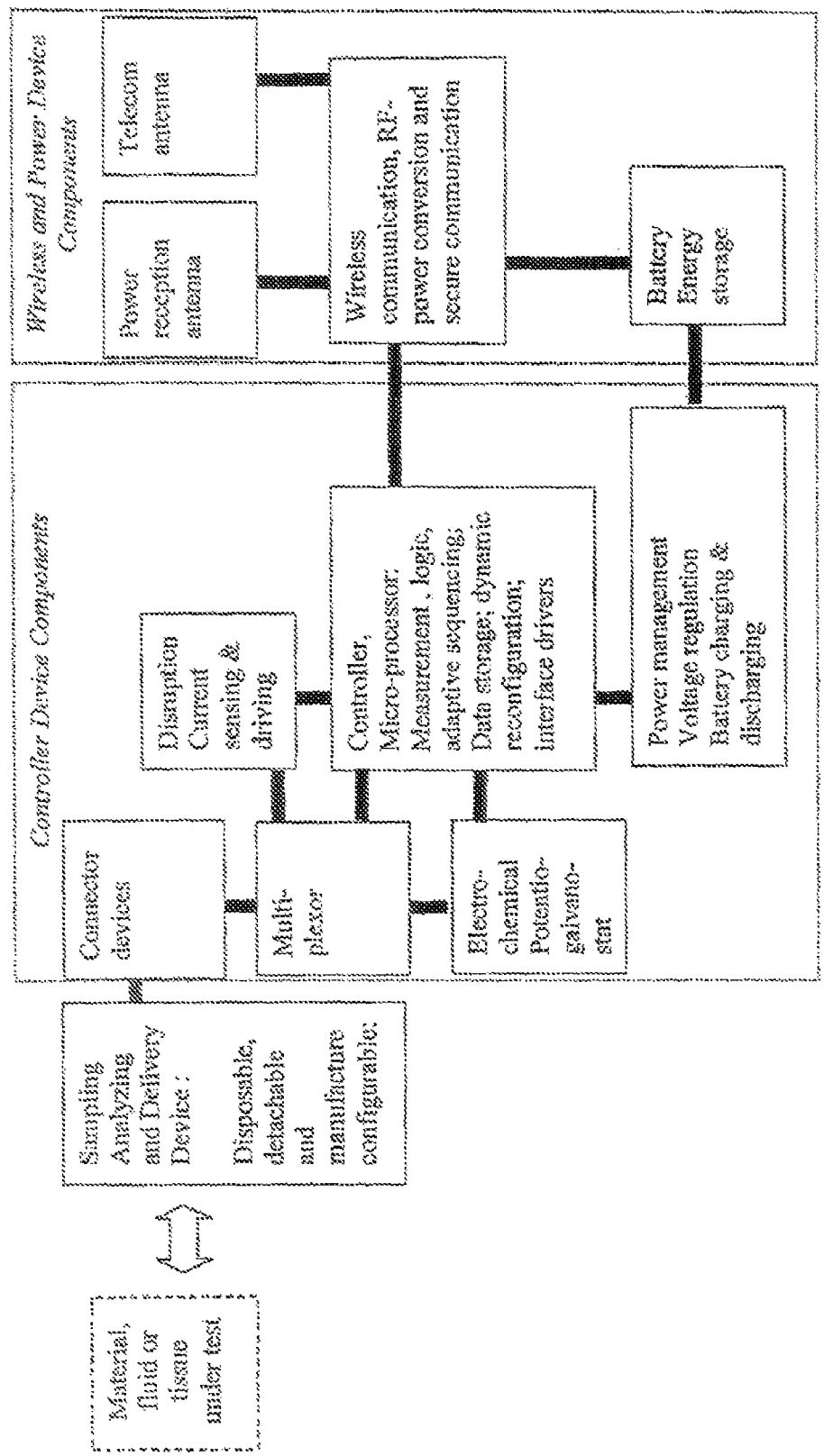
FIG. 20 is a block diagram indicating some components of the controller and wireless communication.

FIG. 20 is a block diagram indicating some components of the controller and wireless communication.

In the system, the material, fluid or tissue under test interacts with the sampling analyzing and delivery device that may be disposable, detachable and manufacture configurable.

Controller Device Components comprise Connector devices, a multi-plexor, a Electro-chemical Potentio-galvano-stat, a Disruption Current sensing & driving circuit, a Controller, Micro-processor for measurement, logic, adaptive sequencing, data storage, dynamic reconfiguration and to provide interface drivers, and a power management for voltage regulation and battery charging and discharging.

The Wireless and Power Device Components comprises reception antenna, wireless communications modules, RF power management and battery power storage.

Although the invention has been described in language specific to structural features and/or methodological acts, it is to be understood that the invention defined in the appended claims is not necessarily limited to the specific features or acts described. Rather, the specific features and acts are disclosed as exemplary forms of implementing the claimed invention

INDUSTRIAL APPLICABILITY

In the field of field of therapeutic care and drug deliver there is significant interest is trans-dermal sampling that is minimally invasive and can be used for continuous real-time trace sampling of Interstitial fluid from the viable epidermis.

What is claimed:

1. A device for transdermal sampling comprising:
a flexible substrate;
at least one pair of sample electrodes disposed on the flexible substrate;
an anchor layer covering at least a portion of at least one pair of sample electrodes;
a first pair of electrically conductive paths coupled to the at least one pair of sample electrodes;
a second pair of electrically conductive paths; and
at least one resistive element coupled to the second pair of electrically conductive paths, wherein:
the at least one resistive element is disposed proximate to the at least one pair of sample electrodes and configured to provide a sequence of thermal heating to generate a temperature sufficient to disrupt stratum corneum cells of a subject without damaging the stratum corneum cells to thereby allow interstitial fluid to pass through capillary openings formed through the stratum corneum cells and into contact with the at least one pair of sample electrodes.

2. The device according to claim 1, wherein the anchor layer comprises an enzyme.

3. The device according to claim 2, wherein the enzyme is selected from the group consisting of glucose oxidase and lactate oxidase.

4. The device according to claim 1, wherein the at least one resistive element has a resistance of about 50 Ohms to about 200 Ohms.

5. The device according to claim 1, wherein the sequence of thermal heating are created by applying voltage pulses to the at least one resistive element that are about 2 volts or less and for less than about 1 second.

6. The device according to claim 1, wherein the flexible substrate comprises a cavity and the interstitial fluid is collected into the cavity.

7. The device according to claim 6, wherein the at least one pair of sample electrodes are at least partially disposed in the cavity.

8. The device according to claim 1, wherein the flexible substrate comprises a polymer.

9. The device according to claim 1, wherein the flexible substrate comprises a multilayer polymeric metal laminate structure.

10. A method for transdermal sampling comprising:
affixing a device for transdermal sampling to the stratum corneum layer of a subject, wherein the device for transdermal sampling comprises:
a flexible substrate;
at least one pair of sample electrodes disposed on the flexible substrate;
an anchor layer covering at least a portion of at least one pair of sample electrodes;
a first pair of electrically conductive paths coupled to the at least one pair of sample electrodes;
a second pair of electrically conductive paths; and
at least one resistive element coupled to the second pair of electrically conductive paths, wherein:

the at least one resistive element is disposed proximate to the at least one pair of sample electrodes and configured to provide a sequence of thermal heating to generate a temperature sufficient to disrupt stratum corneum cells of a subject without damaging the stratum corneum cells to thereby allow interstitial fluid to pass through capillary openings formed through the stratum corneum cells and into contact with the at least one pair of sample electrodes; and applying voltage pulses to the at least one resistive element via the second pair of electrically conductive paths to generate the temperature sufficient to disrupt the stratum corneum cells, wherein the voltage pulses are about 2 volts or less and are of a duration of 1 second or less.

11. The method according to claim 10, wherein the anchor layer comprises an enzyme.

12. The method according to claim 11, wherein the enzyme is selected from the group consisting of glucose oxidase and lactate oxidase.

13. The method according to claim 10, wherein the at least one resistive element has a resistance of about 50 Ohms to about 200 Ohms.

14. The method according to claim 10 further comprising:
measuring an electrical property generated across at least one pair of sample electrodes; and
correlating the measured electrical property to a biological condition.

15. The method according to claim 14, further comprising delivering a material from a cavity within the device for transdermal sampling to the interstitial fluid.

16. The method according to claim 15, further comprising analyzing the interstitial fluid for efficacy of the material.

17. The method according to claim 14, further comprising:
determining whether the correlated biological condition is normal; and
generating a signal when the correlated biological condition is abnormal.

18. The method according to claim 17, wherein the determining whether the correlated biological condition is normal comprises comparing the correlated biological condition to a normal healthy baseline condition.

19. The method according to claim 14, wherein the biological condition is related to the amount of a targeted biomolecule present in the interstitial fluid, wherein the targeted bio molecule is selected from the group consisting of glucose and lactate.

20. The method according to claim 14, wherein the electrical property is current.

21. The method according to claim 10 further comprising:
controlling the application of voltage pulses with a controller; and
communicating information between the controller and a remote device.

* * * * *